(12) United States Patent
Pillai et al.

(10) Patent No.: US 7,676,264 B1
(45) Date of Patent: Mar. 9, 2010

(54) SYSTEMS AND METHODS FOR USE BY AN IMPLANTABLE MEDICAL DEVICE FOR EVALUATING VENTRICULAR DYSSYNCHRONY BASED ON T-WAVE MORPHOLOGY

(75) Inventors: Ajit Pillai, Sunnyvale, CA (US); Mihir Naware, San Jose, CA (US); Dorin Panescu, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 326 days.

(21) Appl. No.: 11/734,850

(22) Filed: Apr. 13, 2007

(51) Int. Cl.
*A61N 1/00* (2006.01)

(52) U.S. Cl. ......................................................... 607/9

(58) Field of Classification Search ................. 600/509, 600/510; 607/4, 9–28
See application file for complete search history.

(56) References Cited

U.S. PATENT DOCUMENTS

| | | | |
|---|---|---|---|
| 5,139,028 A | 8/1992 | Steinhaus et al. | |
| 5,476,483 A | 12/1995 | Bornzin et al. | |
| 6,128,534 A | 10/2000 | Park et al. | |
| 6,129,744 A | 10/2000 | Boute | |
| 6,249,705 B1 | 6/2001 | Snell | |
| 6,438,409 B1 | 8/2002 | Malik et al. | |
| 6,456,880 B1 | 9/2002 | Park et al. | |
| 6,473,647 B1 | 10/2002 | Bradley | |
| 6,480,733 B1 | 11/2002 | Turcott | |
| 6,512,952 B2 | 1/2003 | Stahmann et al. | |
| 6,512,953 B2 | 1/2003 | Florio et al. | |
| 6,522,923 B1 | 2/2003 | Turcott | |
| 6,527,729 B1 | 3/2003 | Turcott | |
| 6,572,557 B2 | 6/2003 | Tchou et al. | |
| 6,628,988 B2 | 9/2003 | Kramer et al. | |
| 6,643,546 B2 | 11/2003 | Mathis et al. | |
| 6,643,548 B1 | 11/2003 | Mai et al. | |
| 6,650,931 B1 | 11/2003 | McClure | |
| 6,658,292 B2 | 12/2003 | Kroll et al. | |
| 6,671,549 B2 | 12/2003 | Van Dam et al. | |
| 6,711,439 B1 | 3/2004 | Bradley et al. | |
| 6,741,885 B1 | 5/2004 | Park et al. | |
| 6,748,261 B1 | 6/2004 | Kroll | |
| 6,853,861 B1 | 2/2005 | Obel et al. | |
| 6,922,587 B2 | 7/2005 | Weinberg | |
| 6,942,622 B1 | 9/2005 | Turcott | |
| 7,069,069 B2 | 6/2006 | Fishler et al. | |
| 7,072,715 B1 * | 7/2006 | Bradley ........................ | 607/17 |
| 7,107,093 B2 | 9/2006 | Burnes | |
| 7,113,823 B2 | 9/2006 | Yonce et al. | |
| 2004/0158165 A1 | 8/2004 | Yonce et al. | |
| 2006/0189876 A1 * | 8/2006 | Couderc et al. ............. | 600/516 |

(Continued)

*Primary Examiner*—George Manuel
*Assistant Examiner*—Robert N Wieland
(74) *Attorney, Agent, or Firm*—Steven M. Mitchell; Theresa A. Takeuchi

(57) ABSTRACT

Techniques are provided for detecting and evaluating ventricular dyssynchrony based on morphological features of the T-wave and for controlling therapy in response thereto. For example, the number of peaks in the T-wave, the area under the peaks, the number of points of inflection, and the slope of the T-wave can be used to detect ventricular dyssynchrony and evaluate its severity. As ventricular dyssynchrony often arises due to heart failure, the degree of dyssynchrony may also be used as a proxy for tracking the progression of heart failure. Pacing therapy is automatically and adaptively adjusted based on the degree of ventricular dyssynchrony so as to reduce the dyssynchrony and thereby improve cardiac function.

52 Claims, 14 Drawing Sheets

U.S. PATENT DOCUMENTS

2007/0135722 A1* 6/2007 Lin .......................... 600/509
2007/0208264 A1* 9/2007 Hardahl et al. ............. 600/510
2008/0004665 A1* 1/2008 McCabe et al. ............. 607/9

* cited by examiner

SYSTEMS AND METHODS FOR USE BY AN IMPLANTABLE MEDICAL DEVICE FOR EVALUATING VENTRICULAR DYSSYNCHRONY BASED ON T-WAVE MORPHOLOGY

FIELD OF THE INVENTION

The invention generally relates to implantable medical devices, such as pacemakers or implantable cardioverter/defibrillators (ICDs), and in particular to techniques for evaluating ventricular dyssynchrony within heart failure patients and for controlling therapy in response thereto.

BACKGROUND OF THE INVENTION

Heart failure is a debilitating disease in which abnormal function of the heart leads in the direction of inadequate blood flow to fulfill the needs of the tissues and organs of the body. Typically, the heart loses propulsive power because the cardiac muscle loses capacity to stretch and contract. Often, the ventricles do not adequately eject or fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive. As heart failure progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles (particularly the left ventricle) to grow in thickness in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output. A particularly severe form of heart failure is congestive heart failure (CHF) wherein the weak pumping of the heart leads to build-up of fluids in the lungs and other organs and tissues.

Heart failure is often associated with electrical signal conduction defects within the heart. The natural electrical activation system through the heart involves sequential events starting with the sino-atrial (SA) node, and continuing through the atrial conduction pathways of Bachmann's bundle and internodal tracts at the atrial level, followed by the atrio-ventricular (AV) node, the Bundle of His, the right and left bundle branches, with final distribution to the distal myocardial terminals via the Purkinje fiber network. Any of these conduction pathways may potentially be degraded. A common conduction defect arising in connection with CHF is left bundle branch block (LBBB). The left bundle branch forms a broad sheet of conduction fibers along the septal endocardium of the left ventricle and separates into two or three indistinct fascicles. These extend toward the left ventricular apex and innervate both papillary muscle groups. The main bundle branches are nourished by septal perforating arteries. In a healthy heart, electrical signals are conducted more or less simultaneously through the left and right bundles to trigger synchronous contraction of both the septal and postero-lateral walls of the left ventricle. LBBB occurs when conduction of electrical signals through the left bundle branch is delayed or totally blocked, thereby delaying delivery of the electrical signal to the left ventricle and altering the sequence of activation of that ventricle. The impulse starts in the right ventricle (RV) and crosses the septum causing the interventricular septum to depolarize and hence, contract, first. The electrical impulse continues to be conducted to the postero-lateral wall of the left ventricle causing its activation and depolarization but, due to an inability to use the native conduction system, this activation and contraction is delayed. As such, the posterolateral wall of the left ventricle (LV) only starts to contract after the interventricular septum has completed its contraction and is starting to relax. LBBB thus results in an abnormal activation of the left ventricle inducing desynchronized ventricular contraction (i.e. ventricular dyssynchrony) and impairment in cardiac performance.

Degeneration of the electrical conduction system as manifested by LBBB or other conduction defects may come from an acute myocardial infarction but is usually associated with the degeneration as a result of chronic ischemia, left ventricular hypertension, general aging and calcification changes and stretch, especially any form of cardiac myopathy that results in overt CHF. Present treatments are directed towards correcting this electrical correlate by pacing on the left side of the heart and/or pacing on both sides of the left ventricle (lateral-posterior wall and septum) to improve contractile coordination. One particular technique for addressing LBBB is cardiac resynchronization therapy (CRT), which seeks to normalize asynchronous cardiac electrical activation and the resultant asynchronous contractions by delivering synchronized pacing stimulus to both sides of the ventricles using pacemakers or ICDs equipped with biventricular pacing capability, i.e. CRT seeks to reduce or eliminate ventricular dyssynchrony. Ventricular stimulus is synchronized so as to help to improve overall cardiac function. This may have the additional beneficial effect of reducing the susceptibility to life-threatening tachyarrhythmias. With CRT, pacing pulses are delivered directly to the left ventricle in an attempt to ensure that the left ventricular myocardium will contract more uniformly. CRT may also be employed for patients whose nerve conduction pathways are corrupted due to right bundle branch block (RBBB) or due to other problems such as the development of scar tissue within the myocardium following a myocardial infarction. CRT and related therapies are discussed in, for example, U.S. Pat. No. 6,643,546 to Mathis, et al., entitled "Multi-Electrode Apparatus And Method For Treatment Of Congestive Heart Failure"; U.S. Pat. No. 6,628,988 to Kramer, et al., entitled "Apparatus And Method For Reversal Of Myocardial Remodeling With Electrical Stimulation"; and U.S. Pat. No. 6,512,952 to Stahmann, et al., entitled "Method And Apparatus For Maintaining Synchronized Pacing".

With conventional CRT, an external Doppler-echocardiography system may be used to noninvasively assess cardiac function. It can also be used to assess the effectiveness of any programming changes on overall cardiac function. Then, biventricular pacing control parameters of the pacemaker or ICD are adjusted by a physician using an external programmer in an attempt to synchronize the ventricles and to optimize patient cardiac function. For example, the physician may adjust the interventricular pacing delay, which specifies the time delay between pacing pulses delivered to the right and left ventricles, in an attempt to maximize cardiac output. To assess the effectiveness of any programming change, Doppler-echocardiography, impedance cardiography or some other independent measure of cardiac function is utilized. However, this evaluation and programming requires an office visit and is therefore a timely and expensive process. It also restricts the evaluation to a resting state, commonly with the patient in a supine position. As such, the system is not necessarily optimized for activity, for the upright position, for other times of day since there may also be a circadian rhythm to cardiac function. Also, heart rate and blood pressure have diurnal or circadian variations. Moreover, when relying on any external hemodynamic monitoring system, the control parameters of the pacemaker or ICD cannot be automatically adjusted to respond to on-going changes in patient cardiac function.

Accordingly, it is desirable to configure an implanted device to automatically and frequently evaluate the degree of ventricular dyssynchrony within a patient, particularly within those suffering from heart failure, and to automatically adjust the CRT pacing parameters to reduce the degree of dyssynchrony and improve cardiac output. Heretofore, various techniques for use by implantable devices for evaluating ventricular dyssynchrony have exploited the relative timing of left and right ventricular depolarization events within an intracardiac electrogram (IEGM) signal sensed by the device. In this regard, mechanical contraction of the ventricles is manifest within the IEGM as an electrical depolarization event referred to as the QRS-complex. The QRS-complex is usually preceded by a P-wave, which corresponds to the electrical depolarization of the atria. The QRS-complex is usually followed by a T-wave, which corresponds to the electrical repolarization of the ventricles. (The repolarization of the atria typically generates an electrical signal too weak to be reliably detected.) As already explained, ventricular dyssynchrony results from asynchronous mechanical contractions of the ventricles, i.e. the left and right ventricles do not contract at precisely the same time. As such, the electrical depolarization signals generated within the left and right ventricles are likewise asynchronous. That is, the QRS-complex of the left ventricle is no longer synchronized with that of the right ventricle. Accordingly, ventricular dyssynchrony can be detected by separately detecting the depolarization of the LV and the depolarization of the RV, i.e. by separately detect both an LV QRS-complex and an RV QRS-complex. Any significant time delay therebetween is indicative of ventricular dyssynchrony. CRT is then performed in an effort to reduce that dyssynchrony, i.e. pacing pulses are separately applied to the left and right ventricles subject to an interventricular pacing delay set by the device in an attempt to re-synchronize the ventricles.

Techniques for detecting ventricular dyssynchrony based on QRS-complexes and for delivering CRT in response thereto are set forth in some of the above-cited patents. However, problems remain. One particular problem with QRS-complex-based techniques is that they are optimal only if the ventricles contract due to intrinsic electrical stimulation (i.e. the stimulation reaches the ventricles along the aforementioned natural AV conduction pathways.) If the ventricles are being paced by the implanted device, then the QRS-complex morphology within the IEGM can change greatly affecting the performance of the QRS-complex-based technique. Rather, an evoked response (ER) appears within the IEGM, which is representative of the depolarization of the ventricular myocardium due to the application of an artificial pacing pulse. The shape of the ER typically differs from that of the QRS-complex. Moreover, time delays between ERs cannot typically be used to detect ventricular dyssynchrony since the ERs are themselves synchronized with the pacing pulses, which are artificially applied. This presents a significant problem during CRT, since ventricular pacing pulses are preferably delivered for each heartbeat. Hence, during CRT, it would not be optimal to use QRS-complex-based dyssynchrony detection techniques to evaluate the degree of ventricular dyssynchrony to, e.g., verify that CRT is effective or to adjust the interventricular pacing delay. It is possible to temporarily suspend CRT in order to allow the ventricles to beat naturally so that the degree of dyssynchrony can again be evaluated via an analysis of the QRS-complexes. However, this technique, in addition to being undesired clinically, does not necessarily provide an indication of the amount of dyssynchrony, if any, occurring during actual delivery of CRT pacing.

Accordingly, it is desirable to provide techniques for detecting ventricular dyssynchrony that do not necessarily require detection of QRS-complexes and it is to this end that the invention is generally directed.

Heretofore, at least some techniques have been developed for controlling CRT or for evaluating ventricular dyssynchrony that do not rely on interventricular delays measured from QRS-complexes. See, for example, U.S. patent application Ser. No. 11/558,194, of Panescu et al., filed Nov. 9, 2006, entitled "Closed-Loop Adaptive Adjustment of Pacing Therapy based on Cardiogenic Impedance Signals Detected by an Implantable Medical Device," which sets forth techniques wherein mechanical interventricular conduction delays are elevated based on a cardiogenic impedance signal. See also, U.S. patent application Ser. No. 11/557,887, of Shelchuk, filed Nov. 8, 2006, entitled "Systems and Methods for Evaluating Ventricular Dyssynchrony Using Atrial and Ventricular Pressure Measurements Obtained by an Implantable Medical Device," which sets forth techniques wherein mechanical interventricular conduction delays are elevated based on atrial and ventricular pressure measurements. See, also, U.S. Pat. No. 7,072,715 to Bradley, entitled "Implantable Cardiac Stimulation Device for and Method of Monitoring Progression or Regression of Heart Disease by Monitoring Evoked Response Features," which exploits certain features of the ER to detect progression or regression of heart disease, though it does not specifically evaluate the degree of ventricular dyssynchrony.

Herein, additional and alternative techniques are provided for evaluating ventricular dyssynchrony and for controlling CRT or other forms of stimulation therapy that do not rely on QRS-complexes.

SUMMARY OF THE INVENTION

In an exemplary embodiment, a method is provided for use with an implantable medical device for detecting and evaluating ventricular dyssynchrony. Briefly, an electrical cardiac signal such as an IEGM is sensed within the patient in which the device is implanted. A ventricular repolarization event (i.e. a T-wave) is sensed within the electrical cardiac signal. At least one morphological feature of the T-wave that is affected by ventricular dyssynchrony is measured, such as the number of peaks within the T-wave or the numerical area under the peaks of the T-wave. Ventricular dyssynchrony, if any, within the patient is then detected based on the morphological feature of the T-wave. In other words, ventricular dyssynchrony is evaluated by exploiting morphological changes in T-waves associated with ventricular dyssynchrony. Since T-waves occur following paced and sensed (i.e. intrinsic) ventricular beats, the T-wave-based ventricular dyssynchrony detection technique may be advantageously exploited at all times within the patient. That is, it need not be deactivated during CRT or other forms of ventricular pacing. The T-wave-based detection technique may be used to supplement other ventricular dyssynchrony detection technique or may be used as a stand-alone technique.

In a first illustrative embodiment, the morphological feature of the T-wave that is exploited to detect ventricular dyssynchrony is the number of peaks or troughs of the T-wave. That is, the implantable device counts the number of peaks or troughs within the T-wave of each heartbeat. The detection of two or more peaks (or two or more troughs) within an individual T-wave is deemed to be indicative of ventricular dyssynchrony. In this regard, the T-wave recorded in a bipolar electrogram from one of the ventricles may contain influences from the repolarization signal coming from the other ventricle. If the RV and LV are contracting asynchronously relative to one another, then the two chambers will likely also depolarize asynchronously. As such, the influence of one ventricle's repolarization would be reflected asynchronously in the T-wave recorded in the other ventricle's electrogram. The superposition of the local T-wave and the influence coming from the other ventricle results in a T-wave with multiple repolarization peaks. That is, the presence of multiple peaks or troughs within the T-waves is an indication of asynchronous mechanical contraction and relaxation of the ventricles and thus is indicative of the presence of ventricular dyssynchrony. Typically, asynchronous contractions of the LV and the RV yield one pair of positive peaks and one pair of corresponding troughs within the T-wave, that is the T-wave is bifurcated. The condition described above is reflective of interventricular dyssynchrony. Either one, or both, ventricles could be affected by intraventricular dyssynchrony. Intraventricular dyssynchrony manifests by significant delays in the depolarization or repolarization of various regions of a ventricle. In a normal heart, typically, all regions of a ventricle depolarize or repolarize within an interval of several tens of ms (e.g. approx. 30 ms). In a failing heart affected by intraventricular dyssynchrony this interval may get close to, or even exceed, 100 ms. Consequently, bipolar electrograms recorded in a ventricle affected by intraventricular dyssynchrony will have T-waves with a fractionated (or split) aspect, as various regions repolarize with significant relative delays. In such circumstances, the fractionated or split T-wave aspect would occur even if the other ventricle is normal.

Hence, the presence of two peaks or two troughs within the T-wave is an indication of at least some amount of ventricular dyssynchrony and also an indication of possible CHF. The time delay between the peaks or troughs can be measured as an indication of the relative severity of the dyssynchrony and the underlying CHF. That is, a larger time delay between peaks or troughs within the T-wave is indicative of a greater severity of dyssynchrony and CHF. Moreover, heart failure that is particularly severe can cause intraventricular dyssynchrony, as explained above, where different portions of a given ventricular chamber contract asynchronously. For example, portions of the LV myocardium near the apex of the LV may contract asynchronously with respect to portions of the LV that are closer to the SA node. Likewise, different portions of the RV may contract asynchronously with respect to other portions of the RV. As such, different portions of the LV and RV may also repolarize asynchronously, resulting in a T-wave that has three or more peaks. Hence, the total number of peaks or troughs can also be used to evaluate the relative severity of ventricular dyssynchrony and CHF. For devices equipped to perform biventricular pacing, the parameters used to control pacing can be automatically adjusted by the device so as to reduce the degree of dyssynchrony by reducing the number of T-wave peaks or troughs or, at least, reducing the time delay therebetween. For example, an interventricular (LV-RV) pacing delay and/or an AV pacing delay may be automatically adjusted.

In a second illustrative embodiment, the morphological feature of the T-wave that is exploited is the numerical area associated with the peaks of the T-wave. In one example, before the onset of ventricular dyssynchrony, the device calculates the numerical area below a portion of the T-wave relative to an isoelectric line for storage as a baseline value. Thereafter, the device periodically evaluates the area under the same portion of the T-wave for comparison against the baseline value. In general, any significant increase in the area of the T-wave relative to the baseline area is indicative of the onset of ventricular dyssynchrony. In one particular embodiment, the device calculates the numerical difference ($\Delta A$) between the area of the peaks of the T-wave (A2+A3) relative to the baseline area (A1). A value of $\Delta A$ that is greater than 0.0 is indicative of ventricular dyssynchrony. Any increase in the value over time is further indicative of progression of ventricular dyssynchrony. In another particular embodiment, the device estimates a relative ratio, Asplit/Abase by calculating the ratio of (A2+A3) to A1 (i.e. (A2+A3)/A1). A value greater than 1.0 is indicative of ventricular dyssynchrony. Any increase in the value over time is likewise indicative of progression of ventricular dyssynchrony. If two or more peaks have developed within the T-wave, the device may separately calculate areas under the different peaks (i.e. A2, A3, etc.), which are then summed for comparison against the baseline area or, in some cases, individually compared against the baseline. In any case, the parameters used to control CRT can be automatically adjusted by the device so as to reduce the degree of dyssynchrony by reducing the area under the T-wave.

In a third illustrative embodiment, the morphological feature of the T-wave that is exploited is the number of inflection points within the T-wave (i.e. the number of points wherein the second numerical derivative of the T-wave signals is zero). The detection of more than three points of inflection within individual T-waves is deemed to be indicative of ventricular dyssynchrony. As noted above, ventricular dyssynchrony can result in an increase in the number of peaks within the T-wave. As such, the number of points of inflection increases as well. A T-wave without ventricular dyssynchrony typically has only three points of inflection. If the T-wave splits into two, then, at least five points of inflection are typically detectable. Otherwise conventional numerical techniques may be used to detect and count the points of inflection. The use of points of inflection is particularly helpful if it is otherwise difficult to count the number of peaks within the T-wave, as may occur if the T-wave becomes fragmented into multiple peaks due to asynchronous contractions of different portions of the LV or different portions of the RV. The parameters used to control biventricular pacing can be automatically adjusted by the device so as to reduce the degree of dyssynchrony by reducing the number of points of inflection in the T-wave.

In a fourth illustrative embodiment, the morphological feature of the T-wave that is exploited is the slope of the T-wave. In one example, before the onset of ventricular dyssynchrony, the device calculates the numerical upslope of a baseline T-wave. This may be performed, e.g. by identifying the starting point of the baseline T-wave (B1 (x,y)) and the peak (B2 (x,y)) of the baseline T-wave, then calculating the slope therebetween (Bslope). Thereafter, the device periodically evaluates the upslope of new T-waves for comparison against the baseline slope. In general, a significant increase in upslope relative to the baseline upslope is indicative of the onset of ventricular dyssynchrony. If the T-wave splits into two, upslope may be calculated based on the first peak of the T-wave. Downslopes may instead be used, i.e. the slope may be measured between the last peak of the T-wave and an end point of the T-wave. In any case, any increase in the magnitude of the upslope or downslope values over time is indicative of progression of ventricular dyssynchrony. The parameters used to control biventricular pacing can be automatically adjusted by the device so as to reduce the degree of dyssynchrony by reducing the upslope and/or downslope of the T-wave.

Other T-wave based morphological parameters may be exploited as well, either alone or in combination. In general, any T-wave parameter that is affected by ventricular dyssynchrony can potentially be used to evaluate ventricular dyssynchrony. For example, any parameter representative of the "fractionation" of the T-wave may potentially be exploited, such as a parameter representative of the frequency of the T-wave. (The number of peaks of the T-wave and the number of points of inflection are also generally representative of T-wave fractionation.) Multiple T-wave morphological parameters may be simultaneously exploited to provide a more robust evaluation of dyssynchrony. The morphology and timing of T-waves simultaneously recorded from the RV and LV can be compared to each other. Even if one of the ventricles is normal, not affected by intraventricular dyssynchrony, the relative timing of the fractionated or split T-wave of the other ventricle can indicate a level of interventricular dyssynchrony. Moreover, T-wave based parameters may be selectively combined with other parameters (such as QRS-complex parameters, pressure measurements, ER parameters, etc.) to provide a still more robust evaluation.

As explained, pacing parameters are preferably adjusted so as to decrease the degree of ventricular dyssynchrony evaluated using T-wave morphological parameters, alone or in combination with other detectable parameters. By adjusting pacing parameters based on, at least, T-wave morphology, the pacing parameters can be promptly adjusted to immediately respond to changes within the heart that affect the T-wave, such as any deterioration in mechanical synchrony arising due to CHF, conduction defects or other ailments such as myocardial infarction or acute cardiac ischemia. Moreover, by adaptively adjusting the pacing parameters based on T-wave morphological parameters, the direction and/or magnitude of the adjustments need not be pre-determined. That is, it need not be known in advance whether a particular pacing parameter should be increased or decreased in response to deterioration in T-wave morphology. Adaptive adjustment allows the direction and magnitude of any adjustments to the pacing parameters to be automatically optimized. Thus, if an initial increase in a particular pacing parameter causes a further deterioration in T-wave morphology, the pacing parameter may then be automatically decreased in an attempt to improve the morphology. If neither an increase nor a decrease in a particular pacing parameter significantly affects T-wave morphology, then a different pacing parameter may be selected for adaptive adjustment. In some implementations, the pacing parameters are adaptively adjusted only when the patient is in a certain predetermined states as determined by activity sensor, posture detectors, etc. In one particular example, adaptive adjustment is only performed if the patient is at rest and in a supine posture. The locations of pacing sites may also be adaptively adjusted based on T-wave morphology.

Thus, a computationally simple procedure for detecting ventricular dyssynchrony and for optimizing pacing parameters to reduce dyssynchrony is provided, which does not require the device to directly evaluate cardiac output or stroke volume or other cardiac performance parameters adversely affected by ventricular dyssynchrony. Preferably, adjustments to the pacing parameters are made substantially in real-time. Trends in ventricular dyssynchrony within the patient may also be identified and tracked to detect, for example, progression of CHF as evidenced, e.g., by an increasing fractionation of the T-wave. Appropriate warnings may be generated for the patient, the physician, or both.

BRIEF DESCRIPTION OF THE DRAWINGS

The above and further features, advantages and benefits of the invention will be apparent upon consideration of the descriptions herein taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of Implantable Medical System

Figure 1:
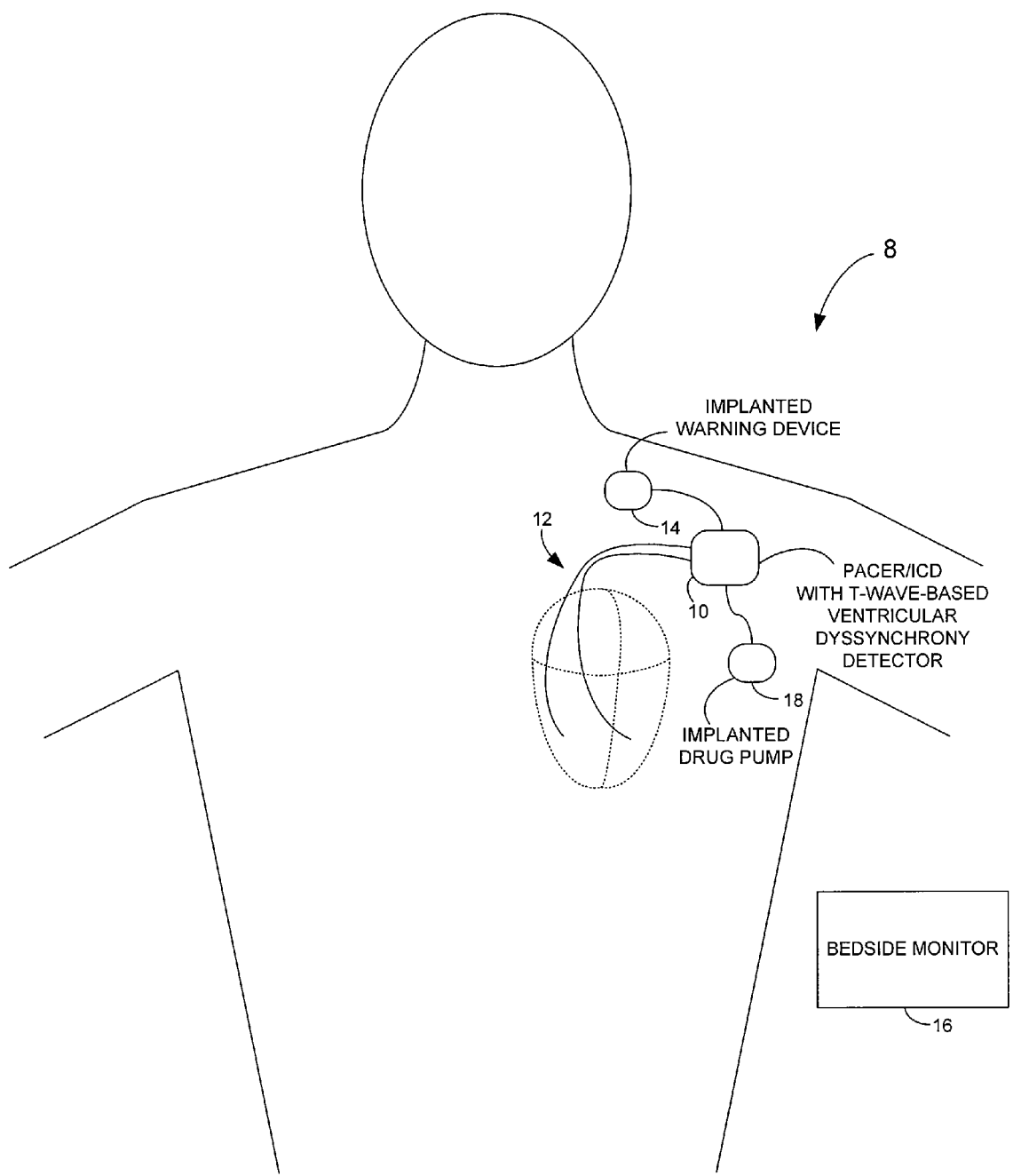
FIG. 1 illustrates pertinent components of an implantable medical system having a pacer/ICD equipped with a T-wave-based ventricular dyssynchrony detector.
Figure 13:
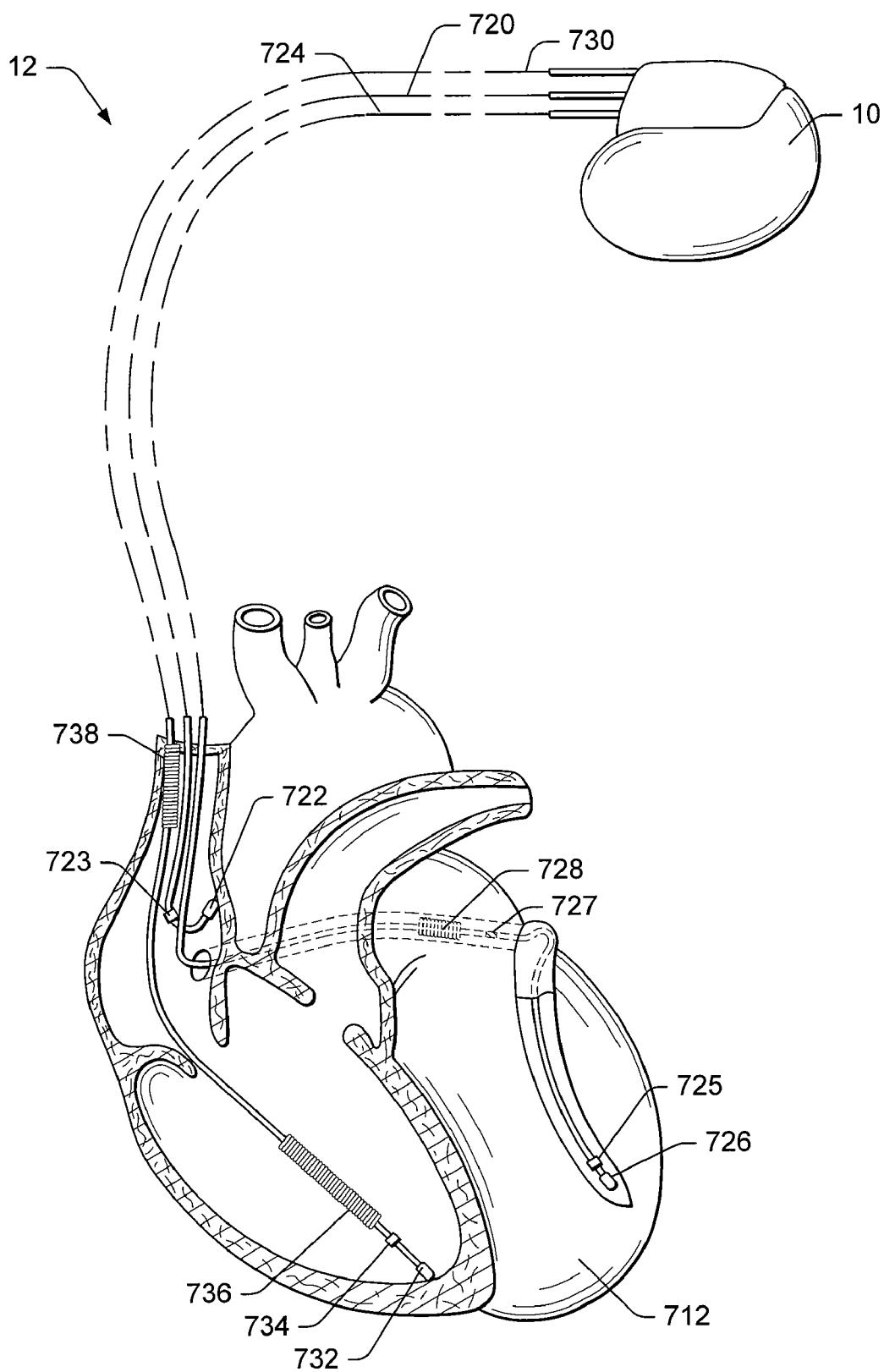
FIG. 13 is a simplified, partly cutaway view, illustrating the pacer/ICD of FIG. 1 along with a complete set of exemplary leads implanted in the heart of a patient.

FIG. 1 illustrates an implantable medical system 8 capable of detecting parameters representative of ventricular dyssynchrony based on T-wave measurements and also for controlling delivery of appropriate therapy in response thereto. To this end, a pacer/ICD 10 (or other implantable medical device) receives IEGM signals or other electrical cardiac signals from a set of cardiac pacing/sensing leads 12. In FIG. 1, only two leads are shown. A more complete set of leads is illustrated in FIG. 13 (described below). T-waves are detected within the IEGM signals and selected morphological parameters are measured, such as the number of peaks, the area under the peaks, the slope, etc. Based on an analysis of the T-wave parameters, the pacer/ICD detects the presence of ventricular synchrony, evaluates its severity, records diagnostic information and issues warnings, if warranted.

For example, if the degree of ventricular dyssynchrony within the patient exceeds an acceptable threshold, warning signals are generated to warn the patient, using either an internal warning device 14 or an external bedside monitor 16. Internal warning device 14 may be a vibrating device or a "tickle" voltage device that, in either case, provides perceptible stimulation to the patient to alert the patient so that the patient may consult a physician. In one example, once the tickle warning is felt, the patient positions an external handheld warning device above his or her chest. The handheld device receives short-range telemetry signals from the implanted device and provides audible or visual verification of the warning signal. The handheld warning device thereby provides confirmation of the warning to the patient, who may be otherwise uncertain as to the reason for the internally generated warning signal. For further information regarding this warning/notification technique, see U.S. patent application Ser. No. 11/043,612, of Kil et al., filed Jan. 25, 2005, entitled "System and Method for Distinguishing Among Ischemia, Hypoglycemia and Hyperglycemia Using an Implantable Medical Device."

If a bedside monitor is provided, the bedside monitor provides audible or visual alarm signals to alert the patient as well as textual or graphic displays. In addition, diagnostic information pertaining to ventricular dyssynchrony is transferred to the bedside monitor or is stored within the pacer/ICD for subsequent transmission to an external programmer (not shown in FIG. 1) for review by a physician or other medial professional. External programmers are typically used only during follow-up sessions with the patient wherein a clinician downloads information from the implanted device, reviews the information and then adjusts the control parameters of the implanted device, if needed, via the programmer. Bedside monitors typically download information more frequently, such as once per evening and can be equipped to relay the most pertinent information to the patient's physician via a communication network. In any case, the physician may then prescribe any other appropriate therapies to address the condition. The physician may also adjust the operation of the pacer/ICD to activate, deactivate or otherwise control any therapies that are automatically applied. The bedside monitor may be directly networked with a centralized computing system, such as the HouseCall™ system of St. Jude Medical, for immediately notifying the physician of any significant deterioration in ventricular synchrony. Networking techniques for use with implantable medical systems are set forth, for example, in U.S. Pat. No. 6,249,705 to Snell, entitled "Distributed Network System for Use with Implantable Medical Devices."

In addition, the pacer/ICD adaptively adjusts pacing parameters so as to reduce or eliminate the amount of ventricular dyssynchrony as determined from the T-wave parameters. Within the exemplary implementations described herein, pacing therapy is adjusted by adaptively adjusting pacing timing parameters, such as the AV delay and the LV-RV delay, so as to reduce the amount of ventricular dyssynchrony. For dual-chamber devices, the AV delay specifies the time delay between a paced or sensed atrial event and a paced ventricular event. For biventricular pacing devices, the LV-RV delay (sometimes also referred to as just the V-V delay) specifies the time delay between a paced or sensed RV event and a paced LV event. (This delay may be negative.) Preferably, the adaptive adjustments are performed substantially in real-time so as to maintain the pacing timing parameters at or near optimal values at all times.

Along with the adaptive adjustment of the pacing parameters, other forms of therapy may also be controlled by the pacer/ICD in response to changes in ventricular dyssynchrony. In this regard, if the implanted system is equipped with a drug pump, appropriate medications may be automatically administered upon detection of a significant deterioration in ventricular dyssynchrony. For example, if the ventricular dyssynchrony arises due to CHF, then various heart failure medications may be delivered directly to the patient via the drug pump, if warranted. Exemplary heart failure medications include angiotensin-converting enzyme (ACE) inhibitors, diuretics, digitalis and compounds such as captopril, enalapril, lisinopril and quinapril. Depending upon the particular medication, alternative compounds may be required for use in connection with an implantable drug pump. Routine experimentation may be employed to identify medications for treatment of heart failure or other conditions that are safe and effective for use in connection with an implantable drug pump. Dosages may be titrated based upon the severity of heart failure. Various techniques may be employed to confirm the detection of ventricular dyssynchrony, heart failure (or other medical conditions) made by the device based on the analysis of the T-wave parameters before drug therapy is delivered.

Additionally, the pacer/ICD performs various standard operations, such as delivering demand based atrial or ventricular pacing, overdrive pacing therapy, antitachycardia pacing (ATP). The pacer/ICD also monitors for atrial or ventricular fibrillation and delivers cardioversion or defibrillation shocks in response thereto.

Hence, FIG. 1 provides an overview of an implantable system capable of detecting ventricular dyssynchrony based on T-wave morphology, and further capable of adaptively controlling pacing therapy in response thereto, for delivering any appropriate warning/notification signals, and for delivering medications, when warranted. Embodiments may be implemented that do not necessarily perform all of these functions. For example, embodiments may be implemented that provide only for detection of ventricular dyssynchrony and generation of warning signals but not for automatic control of pacing therapy. Moreover, systems provided in accordance with the invention need not include all of the components shown in FIG. 1. In many cases, for example, the system will include only a pacer/ICD and its leads. Implantable warning devices and drug pumps are not necessarily implanted. Some implementations may employ an external monitor for displaying warning signals without any internal warning device. These are just a few exemplary embodiments. No attempt is made herein to describe all possible combinations of components that may be provided in accordance with the general principles of the invention. In addition, note that the particular locations of the implanted components shown in FIG. 1 are merely illustrative and may not necessarily correspond to actual implant locations. Although internal signal transmission lines provided are illustrated in FIG. 1 for interconnecting the various implanted components, wireless signal transmission may alternatively be employed.

Overview of T-wave-based Ventricular Dyssynchrony Evaluation Techniques

Figure 2:
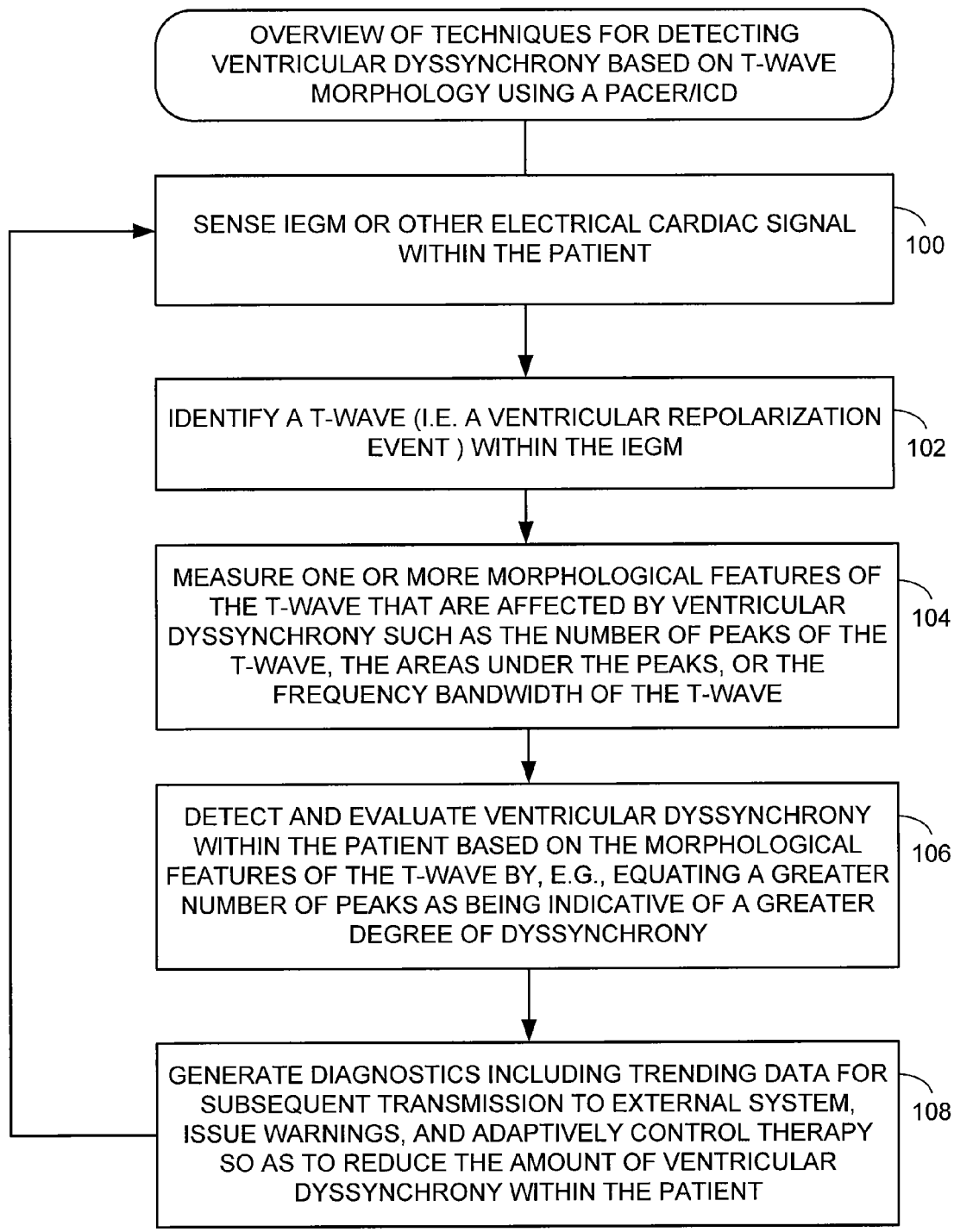
FIG. 2 provides an overview of the T-wave-based method for evaluating ventricular dyssynchrony performed by the system of FIG. 1.

FIG. 2 provides a broad overview of the T-wave-based techniques of the invention for use in detecting and evaluating ventricular dyssynchrony, which may be performed by the pacer/ICD of FIG. 1 or other suitable device. Briefly, beginning at step 100, the pacer/ICD senses an IEGM or other electrical cardiac signal within the patient and, at step 102, identifies a ventricular repolarization event (i.e. a T-wave) within the IEGM, using otherwise conventional techniques. At step 104, the pacer/ICD then measures one or more morphological features of the T-wave that are affected by ventricular dyssynchrony, such as the number of peaks within the event, the areas under the peaks or the frequency bandwidth of the event. Techniques for detecting and measuring various T-wave parameters are discussed in: U.S. patent application Ser. No. 10/603,398, entitled "System and Method for Detecting Cardiac Ischemia Based on T-Waves using an Implantable Medical Device", of Min et al., filed Jun. 24, 2003; U.S. Pat. No. 6,650,931 to McClure, et al., entitled "System and Method of Automatically Determining the Onsets and Ends Of Cardiac Events and Far-Field Signals"; and U.S. patent application Ser. No. 11/394,724, of Ke et al., entitled "System and Method for Detecting Cardiac Ischemia in Real-Time using a Pattern Classifier Implemented within an Implantable Medical Device," filed March 31, 2006. See, also, U.S. Patent Application Serial Number 2004/0077962 of Kroll, published Apr. 22, 2004, entitled "System and Method for Monitoring Blood Glucose Levels Using an Implantable Medical Device." Certain techniques described therein are particularly well suited for detecting T-waves with a high degree of accuracy to permit precise detection of features of the T-wave.

At step 106, the pacer/ICD detects and evaluates ventricular dyssynchrony, if any, within the patient based on the measured morphological features of the T-wave by, e.g., equating a greater number of peaks as being indicative of a greater degree of dyssynchrony. Illustrative techniques are described below wherein T-wave peaks, areas, slopes, and inflection points are exploited, alone or in combination. At step 108, the pacer/ICD then generates diagnostics, issue warnings, and adaptively controls therapy so as to reduce the ventricular dyssynchrony within the patient. In particular, the pacer/ICD may adjust an interventricular pacing delay (i.e. a $V_L$-pulse-$V_R$ pulse pacing delay) to reduce ventricular dyssynchrony. AV pacing delays may also be selectively adjusted (i.e. $A_R$-pulse-$V_R$ pulse and $A_R$-pulse-$V_L$ pulse pacing delays). In at least some cases, adjustment of these parameters may be performed in conjunction with other pacing delay optimization techniques. See, for example, techniques described in the above-cited patent application of Panescu et al., (11/558,194). See, also, techniques set forth in U.S. patent application Ser. No. 10/928,58, of Bruhns et al., filed Aug. 27, 2004, entitled "System and Method for Determining Optimal Atrioventricular Delay based on Intrinsic Conduction Delays"; U.S. patent application Ser. No. 11/199,619, filed Aug. 8, 2005, of Gill et al., entitled "System and Method for Determining Preferred Atrioventricular Pacing Delay Values Based On Intracardiac Electrogram Signals"; and U.S. patent application Ser. No. 11/366,930, of Muller et al., filed Mar. 1, 2006, entitled "System and Method for Determining Atrioventricular Pacing Delay Based on Atrial Depolarization". Other therapeutic techniques may be employed that do not necessarily involve adjusting pacing parameters. See, for example, U.S. patent application Ser. No. 11/136,791 of Kroll et al., filed May 25, 2005, entitled "Synaptic Pacing for Treating Cardiac Conduction Defects Using an Implantable Medical Device."

At step 108, the pacer/ICD also records appropriate diagnostic information including values of the particular T-wave morphological parameters that have been detected. Trend information pertaining to changes in the various parameters may also be stored. If the pacer/ICD is so equipped, histogram-based techniques for reducing the amount of data that needs to be stored for trending purposes may be advantageously employed. See, for example, techniques described in U.S. patent application Ser. No. 11/397,066, of Koh, filed Apr. 3, 2006, entitled "HF Trending Parameter for Screening Out Dilated Cardiomyopathy by Circadian Based R-R Histogram Deviation from the Daily Mean". As already explained, the diagnostic data may be transmitted to an external device, such as a bedside monitor or external programmer for subsequent review by a clinician. Warning signals may be generated in response to any significant increase in ventricular dyssynchrony, which may be indicative of progression of heart failure or other cardiovascular diseases.

As noted, ventricular dyssynchrony may arise due to heart failure and hence any worsening of ventricular dyssynchrony might be indicative of progression of heart failure. Depending upon the capabilities of the pacer/ICD, heart failure may be corroborated by other suitable detection techniques. See, for example, U.S. Pat. No. 6,922,587, entitled "System and Method for Tracking Progression of Left Ventricular Dysfunction Using Implantable Cardiac Stimulation Device", U.S. Pat. No. 6,942,622, entitled "Method For Monitoring Autonomic Tone", U.S. Pat. No. 6,748,261, cited above, U.S. Pat. No. 6,741,885, entitled "Implantable Cardiac Device For Managing The Progression Of Heart Disease And Method", U.S. Pat. No. 6,643,548, entitled "Implantable Cardiac Stimulation Device For Monitoring Heart Sounds To Detect Progression And Regression Of Heart Disease And Method Thereof", U.S. Pat. No. 6,572,557, entitled "System And Method For Monitoring Progression Of Cardiac Disease State Using Physiologic Sensors", U.S. Pat. No. 6,527,729, entitled "Method For Monitoring Patient Using Acoustic Sensor", U.S. Pat. No. 6,512,953, entitled "System And Method For Automatically Verifying Capture During Multi-Chamber Stimulation" and U.S. Pat. No. 6,480,733, entitled "Method For Monitoring Heart Failure", each assigned to Pacesetter, Inc. See, also, U.S. patent application Ser. No. 11/014,276, filed Dec. 15, 2004, of Bornzin et al., entitled "System and Method for Predicting a Heart Condition Based on Impedance Values Using an Implantable Medical Device", and U.S. patent application Ser. No. 10/792,305, filed Mar. 2, 2004, entitled "System And Method For Diagnosing And Tracking Congestive Heart Failure Based On The Periodicity Of Cheyne-Stokes Respiration Using An Implantable Medical Device"; and U.S. patent application Ser. No. 11/397,066 of Koh, entitled "QT-Based System and Method for Detecting and Distinguishing Dilated Cardiomyopathy and Heart Failure Using an Implantable Medical Device", also assigned to Pacesetter, Inc.

At step 108, the pacer/ICD also stores diagnostic information pertaining to ventricular dyssynchrony for subsequent transmission to an external system for physician review, including trending information representative of the progression or regression of ventricular dyssynchrony within the patient.

Steps 100-108 are repeated in a closed loop so as to adaptively adjust therapy. Preferably, the adjustments are made substantially in real-time so as to continuously, or at least very frequently, adjust therapy in response to changes in ventricular dyssynchrony as derived from the T-wave parameters or from other sources. This allows the pacer/ICD to respond promptly to changes within the heart of the patient. To achieve real-time or near real-time performance, the pacer/ICD preferably adjusts therapy based only on computationally simple ventricular dyssynchrony measurements derived from the T-wave parameters.

Turning now to FIGS. 3-12, various exemplary techniques for detecting ventricular dyssynchrony based on T-wave morphological parameters, alone or in combination with other parameters will now be described.

Illustrative Examples

Figure 3:
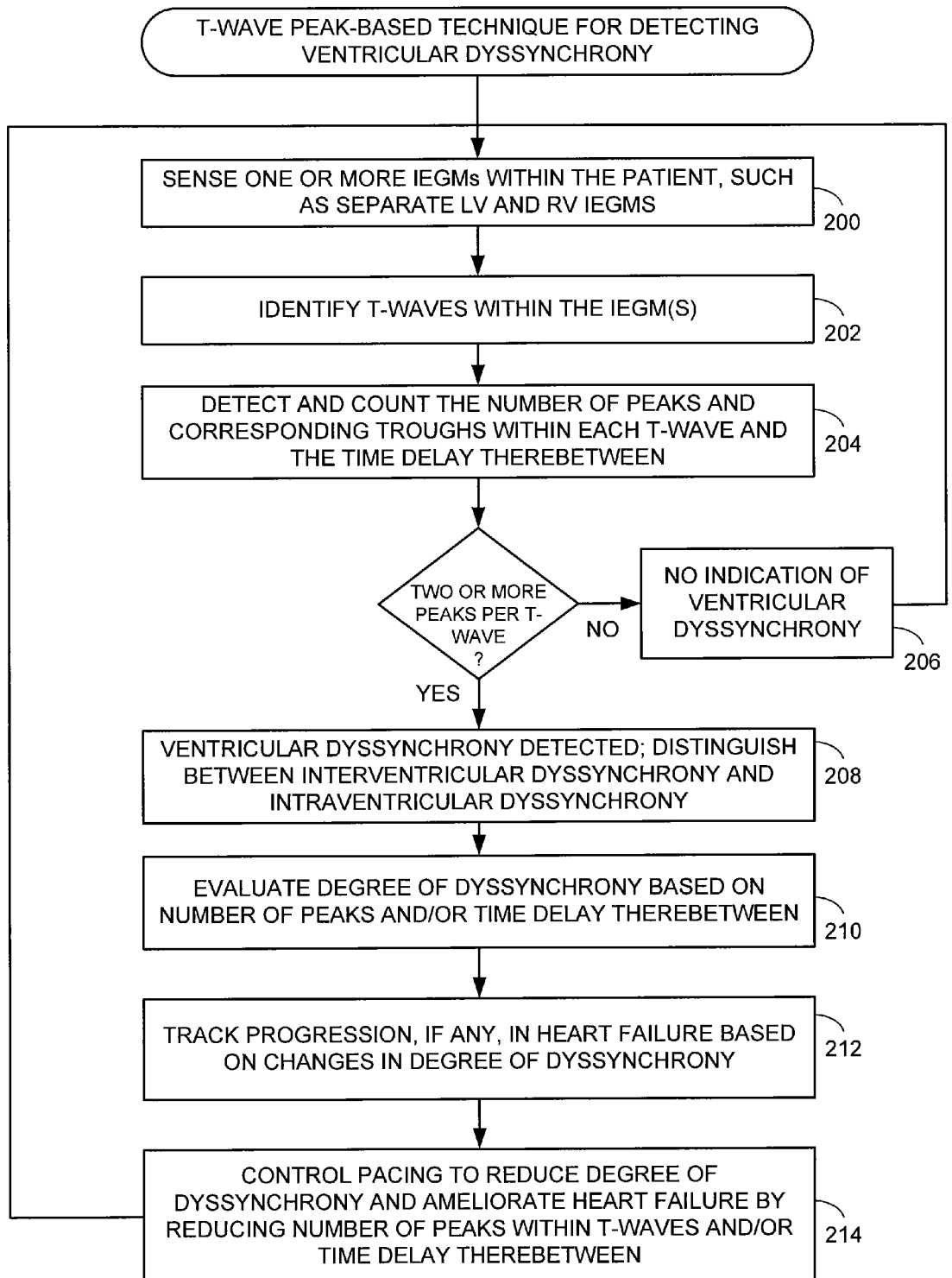
FIG. 3 illustrates a first illustrative embodiment of the general technique of FIG. 2 wherein T-wave peaks are exploited to detect ventricular dyssynchrony.
Figure 4:
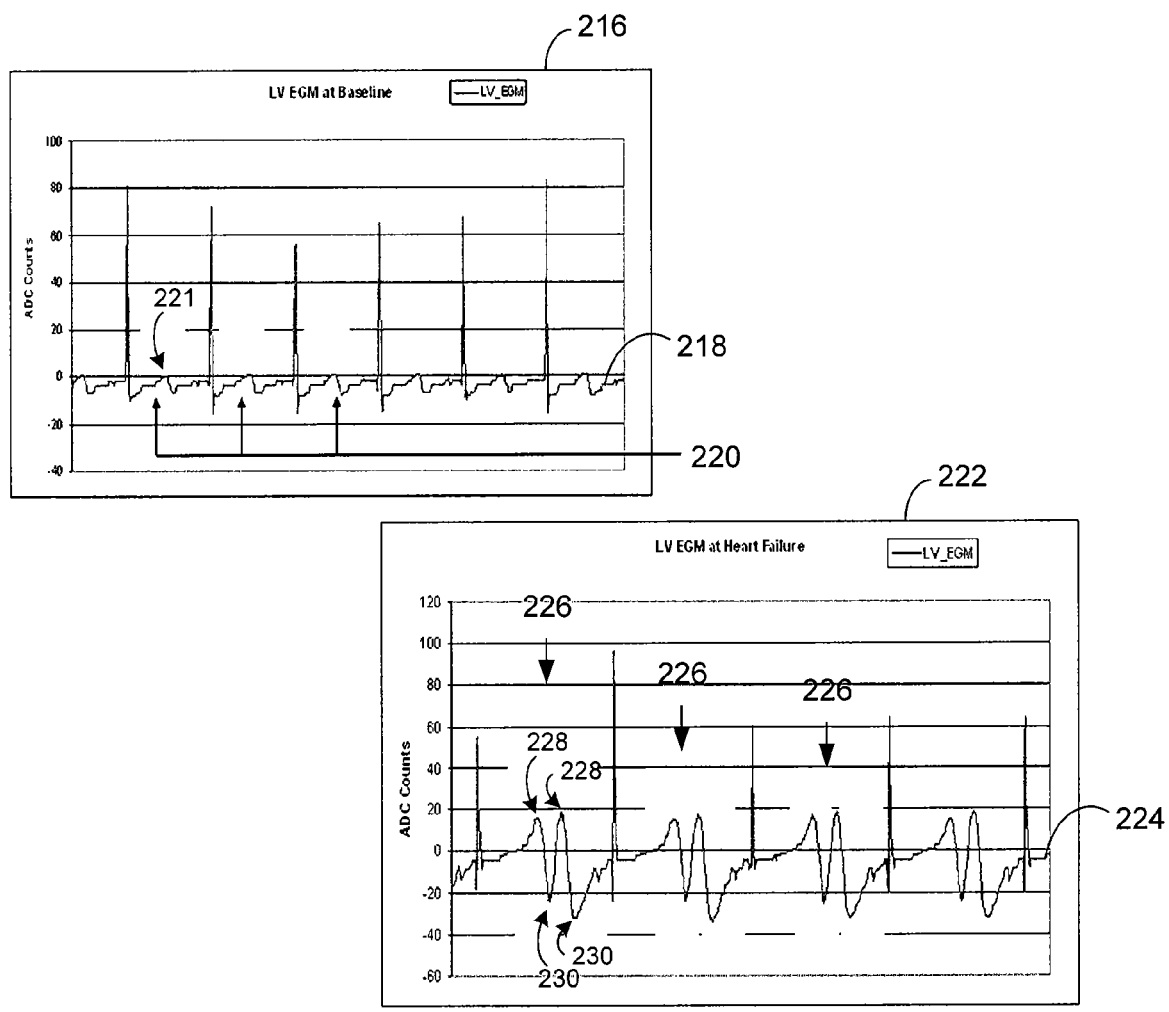
FIG. 4 provides exemplary graphs illustrating the bifurcation of T-wave peaks occurring due to ventricular dyssynchrony, which may be exploited the method of FIG. 3 to detect and evaluate ventricular dyssynchrony.
Figure 5:
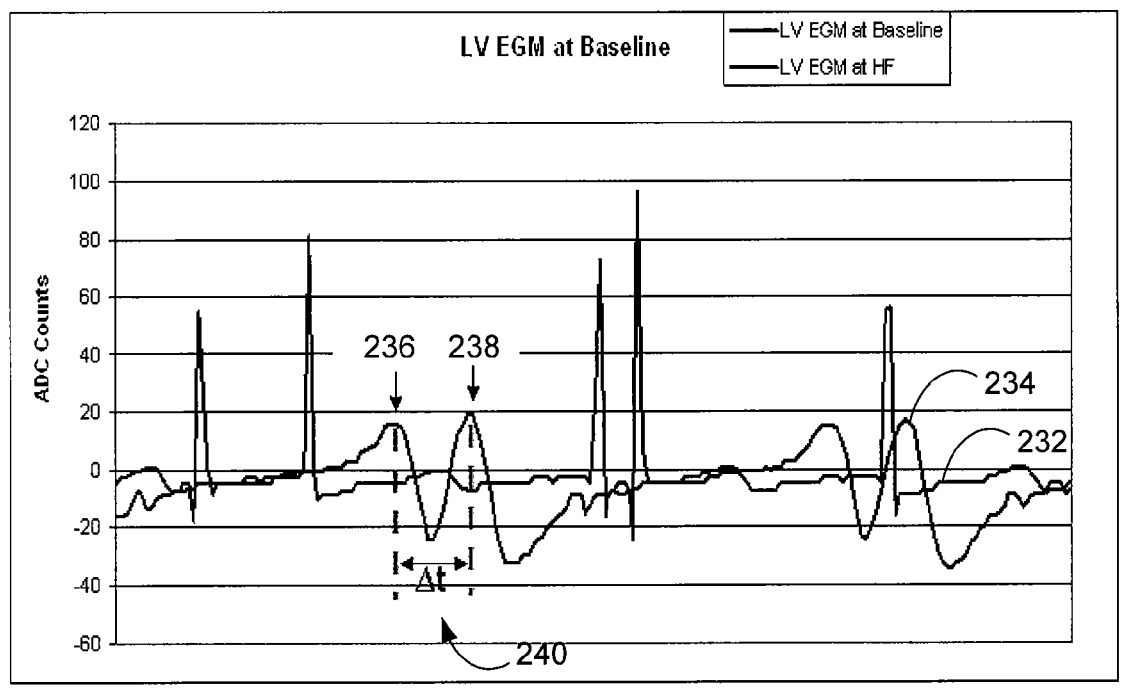
FIG. 5 provides an exemplary graph illustrating an inter-peak T-wave interval, which may be exploited the method of FIG. 3 to detect and evaluate ventricular dyssynchrony.

FIGS. 3-5 illustrate peak-based techniques for evaluating either intraventricular dyssynchrony or interventricular dyssynchrony based on T-wave peaks. Beginning at step 200 of FIG. 3, the pacer/ICD senses the IEGM and, at step 202, identifies T-waves therein. To detect intraventricular dyssynchrony it is sufficient to examine a single IEGM, such as an LV IEGM or an RV IEGM, since the dyssynchrony will be manifest as two or more peaks within a T-wave observed within a single IEGM. For example, intraventricular dyssynchrony within the RV will be manifest by the splitting of the T-wave observed within the RV IEGM into separate peaks. Likewise, intraventricular dyssynchrony within the LV will be manifest by the splitting of the T-wave observed within the LV IEGM into separate peaks. In contrast, to detect interventricular dyssynchrony it is preferable to examine both LV and RV IEGMs, since the dyssynchrony will be manifest by a time delay between the peak of the T-wave observed within the RV IEGM and the peak of the T-wave observed within the RV IEGM. The sensing of separate LV and RV IEGMs is thereby preferred as it readily allows for detection of either intraventricular dyssynchrony within either the LV or the RV as well as the detection of interventricular dyssynchrony between the LV and the RV.

At step 204, the pacer/ICD detects and counts the number of peaks and troughs with individual T-waves. At step 204, the pacer/ICD also measures the time delay between the peaks of each individual T-wave, assuming there are at least two peaks within the T-wave. As noted, the time delay may be between twin T-wave peaks observed within an individual IEGM, such as within just the LV IEGM, or may instead be between T-wave peaks observed within separate IEGMS, i.e. the LV and RV IEGMs. In some cases, both types of time delays are observed and measured. Otherwise conventional techniques can be employed to detect and count the peaks and troughs and to measure the time delay(s) between peaks. For example, the signal amplitude of the LV IEGM can be compared again various thresholds levels to count the number of times the signal crosses the thresholds. Assuming there are at least two peaks within the LV IEGM, the apex of each peak can be identified and the time delay to the next apex within the LV IEGM can then be measured.

Assuming, however, that there is only one peak (or one trough) per T-wave, then no ventricular dyssynchrony is indicated, at step 206. However, if there are two or more peaks (or two or more troughs) per T-wave, then ventricular dyssynchrony is thereby detected, at step 208. At step 208, the pacer/ICD may also identify the type of ventricular dyssynchrony, i.e. whether the dyssynchrony is intraventricular or interventricular. Note that, preferably, ventricular dyssynchrony is not detected based only on a single T-wave having two or more peaks but is instead detected only if some minimum number of T-waves meet the detection criteria. For example, ventricular dyssynchrony may be detected only if X out of Y T-waves meet the detection criteria, where X and Y are programmable values. The pacer/ICD then, at step 210, evaluates the degree of dyssynchrony based on number of peaks and/or the time delay therebetween. A greater time delay between a pair of T-wave peaks observed within an individual IEGM, such as the LV IEGM, is indicative of a greater degree of intraventricular dyssynchrony. A greater time delay between a pair of T-wave peaks observed within separate IEGMs, such as between the LV and RV IEGMs, is indicative of a greater degree of interventricular dyssynchrony. At step 212, the pacer/ICD tracks progression, if any, in heart failure based on changes in degree of ventricular dyssynchrony. In this regard, within a patient known to have heart failure, the degree of ventricular dyssynchrony may be used as a proxy for the severity of heart failure. An increase in ventricular dyssynchrony is deemed to be indicative of progression of heart failure. If the patient has not already been diagnosed with heart failure, the initial detection of ventricular dyssynchrony is indicative of possible heart failure. Accordingly, heart failure detection and evaluation techniques of the type cited above can be activated to determine if the patient indeed has heart failure. Diagnostic data is also stored and suitable warnings are issued so as to notify a physician or other medical professional so he or she can examine the patient to confirm the evaluation of heart failure.

At step 214, the pacer/ICD controls pacing to reduce the degree of dyssynchrony and to ameliorate heart failure by reducing number of peaks (or troughs) within T-waves and/or time delay therebetween. In this regard, the various pacing timing parameters noted above may be adaptively adjusted. That is, typically, at least the AV and LV-RV timing parameters are adjusted. Advantageously, the direction and magnitude of the adjustment need not be known in advance. Rather, the pacer/ICD makes an incremental adjustment in one timing parameter in one direction, then determines whether the adjustment improved the ventricular dyssynchrony of the patient or not. If an improvement is gained, the pacer/ICD makes an additional incremental adjustment in that timing parameter in that same direction in an attempt to achieve still further improvement. If the adjustment has an adverse effect on ventricular dyssynchrony, the pacer/ICD makes an incremental adjustment in the same timing parameter but in the opposite direction in an attempt to achieve an improvement in ventricular dyssynchrony. The magnitudes of the adjustments are adaptively varied so as to further optimize the parameter. If the initial adjustment had no effect, the pacer/ICD selects a different timing parameter to adjust. Once a particular parameter is optimized, the pacer/ICD can select a different parameter. For example, once AV delay has been optimized, LV-RV may then be optimized. The range within which the parameters are automatically adjusted can be restricted via device programming to ensure that the parameters remain within acceptable bounds.

Various additional techniques and strategies for adaptively optimizing pacing parameters may be employed, where appropriate, to supplement or enhance the techniques described herein. Examples are set forth in U.S. patent application Ser. No. 11/231,081, filed Sep. 19, 2005, of Turcott, entitled "Rapid Optimization of Pacing Parameters"; U.S.

patent application Ser. No. 11/199,619, filed Aug. 8, 2005, of Gill et al, entitled "AV Optimization Using Intracardiac Electrogram"; U.S. patent application Ser. No. 11/366,930, of Muller et al., filed Mar. 1, 2006, entitled "System and Method for Determining Atrioventricular Pacing Delay based on Atrial Repolarization"; U.S. patent application Ser. No. 10/928,586, of Bruhns et al., entitled "System and Method for Determining Optimal Atrioventricular Delay based on Intrinsic Conduction Delays", filed Aug. 27, 2004; and U.S. Pat. No. 6,522,923 to Turcott, entitled "Methods, Systems and Devices for Optimizing Cardiac Pacing Parameters Using Evolutionary Algorithms." See, also, the adaptive adjustment techniques described in the above-cited patent application of Panescu et al., (Ser. No. 11/558,194).

The locations of pacing sites may also be adaptively adjusted based on T-wave morphology. In one particular example, the pacer/ICD is equipped with N electrodes in the RV, where N is an arbitrary number of electrodes. The pacer/ICD evaluates the degree of ventricular dyssynchrony arising when unipolar pacing is performed using each RV electrode, i.e. $RV_1$-case, $RV_2$-case, $RV_3$-case, etc. The pacer/ICD then selects the particular RV electrode that achieves the least amount of ventricular dyssynchrony for use in performing further pacing. Once optimal pacing sites are chosen, CRT timing parameters may be optimized using the techniques above for use with that particular pacing site. Similarly, the LV lead may carry multiple CRT pacing electrodes. In a similar fashion, optimal pacing configurations can be selected from the electrodes on the LV CRT lead. Yet similarly, combined RV and LV pacing configurations may be selected to reduce ventricular dyssynchrony. Alternatively, all these pacing electrodes can be separately, or individually, distributed on endocardial, epicardial or within myocardial tissue. The electrodes can be carried on separate leads, on multiple leads or implanted individually.

FIG. 4 provides exemplary IEGM signals, which particularly illustrate the fractionation of T-wave morphology arising from intraventricular dyssynchrony due to heart failure. A first graph 216 illustrates a single IEGM 218 at baseline, i.e. an IEGM for a test subject without heart failure and without ventricular dyssynchrony. As can be seen, each heartbeat of the single IEGM has a T-wave 220 with only a single peak 221. A second graph 222 illustrates the single IEGM 224 for a test subject with intraventricular dyssynchrony due to CHF. As can be seen, each heartbeat of the IEGM has a T-wave 226 with multiple peaks. That is, each T-wave of the single IEGM has two positive peaks 228 and two negative troughs 230, which is indicative of intraventricular dyssynchrony. As already explained, if CHF becomes even more severe, still greater fractionation of the T-wave can occur, yielding even more peaks and troughs. Accordingly, a count of the number of peaks and/or troughs is indicative of the degree of ventricular dyssynchrony. Note that the graphs of FIG. 4 and the various other IEGM graphs attached hereto were obtained from sheep test subjects and are merely provided to illustrate aspects of the invention and should not be construed as necessarily being representative of human patient data. Actual human IEGM signals may differ in shape and magnitude from those of the sheep test subjects and may further differ from one patient to another.

FIG. 5 provides exemplary IEGM signals that particularly illustrate the distance between T-wave peaks that may be exploited to evaluate intraventricular dyssynchrony arising due to heart failure. A first IEGM 232 is taken at baseline, i.e. it is the IEGM of a test subject without heart failure and without intraventricular dyssynchrony. As can be seen, each heartbeat of the single IEGM 232 has a T-wave with only a single peak. A second IEGM 234 is taken from a test subject with intraventricular dyssynchrony due to CHF. Each heartbeat of IEGM 234 has a T-wave with multiple peaks 236, 238. The time interval 240 between the peaks ($\Delta T$) is highlighted. This time interval is representative of the severity of intraventricular dyssynchrony and the underlying heart failure. That is, as heart failure progresses the time delay between the peaks tends to increase due to an increasing time delay between depolarization of the left and right ventricles. In the example, $\Delta T$ is about 125 ms. Generally, any value of $\Delta T$ greater than 60 ms is indicative of possible dyssynchrony within human patients. As already explained, further progression of heart failure can result in further fractionation of the T-wave, yielding additional peaks. As such, the pacer/ICD may be configured to evaluate the time delay between the earliest peak and the last peak for use as $\Delta T$. Moreover, a combination of both the total number of peaks and the time delay between first and last peaks may be exploited as a measure of ventricular dyssynchrony. The type of dyssynchrony can also be analyzed by temporal comparison of the timing of T-waves recorded simultaneously in the two ventricles, i.e. recorded within both an LV IEGM and an RV IEGM. Hence, even if the morphology of the T-wave in one of the ventricles is normal, the other ventricle may have a delayed or fractionated T-wave. The relative timing between the peaks of the RV and LV T-waves should not exceed several tens of ms. If prolonged repolarization is seen in one ventricle with respect to the other, severe bundle branch conditions may be present. The CRT device could then adjust therapy to bring the T-waves in closest alignment possible.

Figure 6:
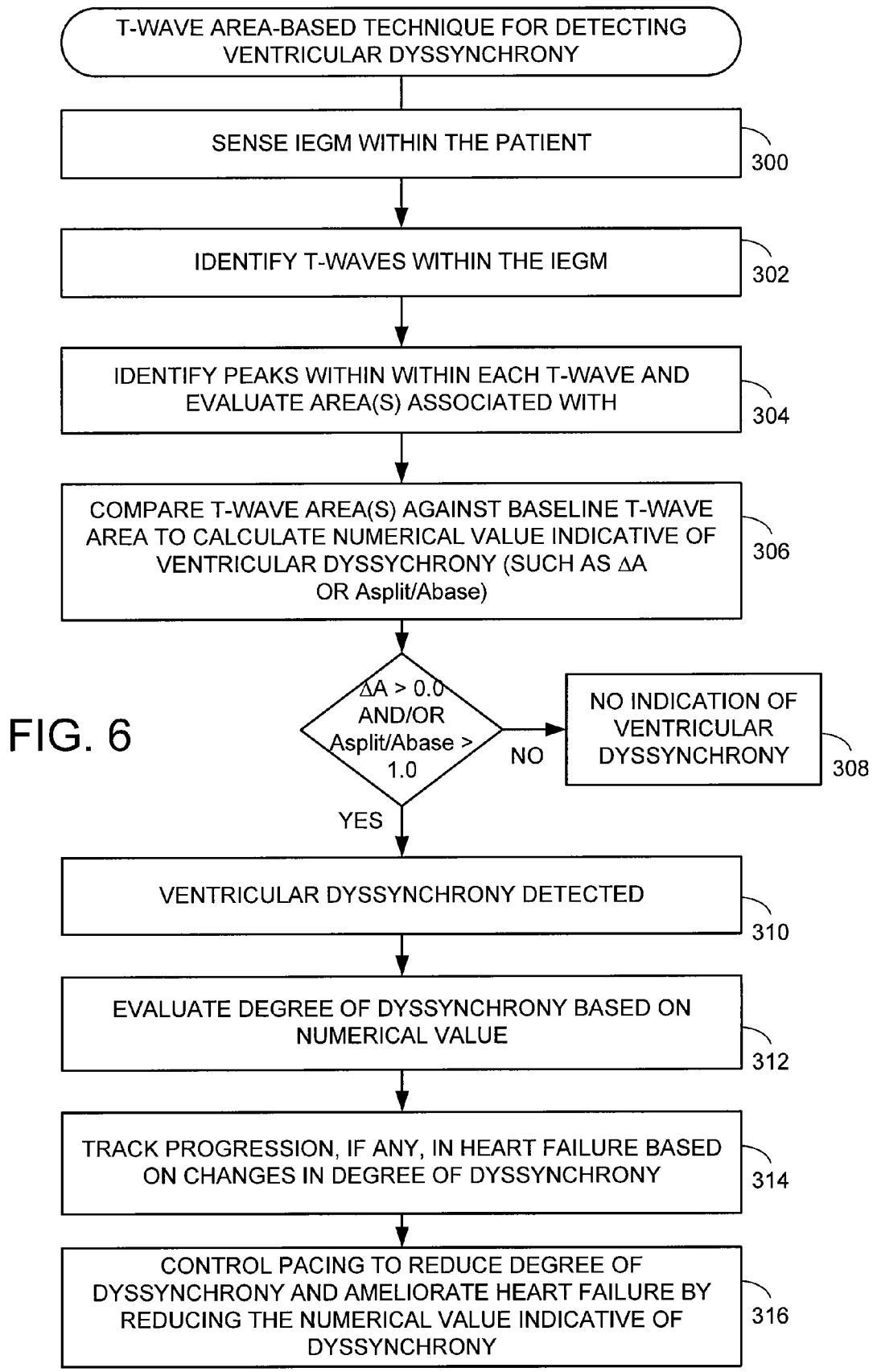
FIG. 6 illustrates a second illustrative embodiment of the general technique of FIG. 2 wherein T-wave areas are exploited to detect ventricular dyssynchrony.
Figure 7:
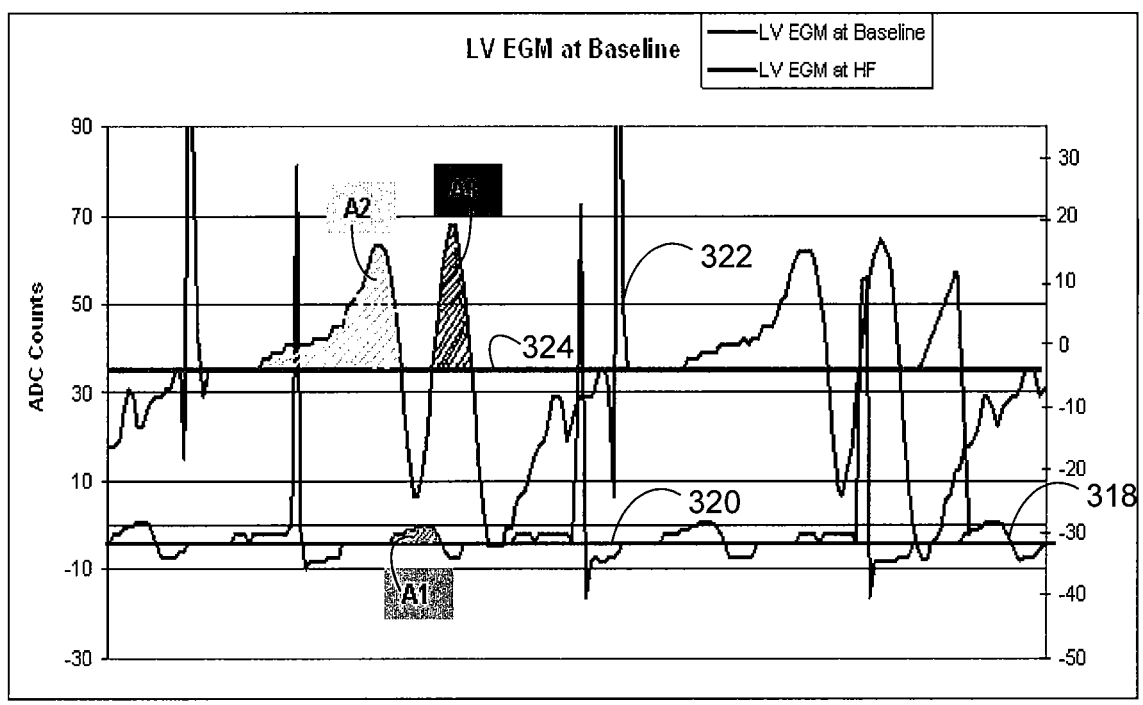
FIG. 7 provides an exemplary graph illustrating T-wave areas, which may be exploited the method of FIG. 3 to detect and evaluate ventricular dyssynchrony.

FIGS. 6-7 illustrate area-based techniques for evaluating ventricular dyssynchrony based on T-wave area. Beginning at step 300 of FIG. 6, the pacer/ICD senses the IEGM and, at step 302, identifies T-waves therein. At step 304, the pacer/ICD detects the peaks within the T-waves and calculates the area (A) under the peaks. Preferably, the area is evaluated relative to an isoelectric baseline voltage. For example, the average elevation of the IEGM signal between the end of one T-wave and the P-wave (or atrial evoked response) of the next heartbeat may be use as the baseline voltage. The pacer/ICD then digitally sums or integrates the signal values of the portions of the IEGM relative to the baseline voltage. If the T-wave is bifurcated into multiple peaks, the pacer/ICD preferably separately calculates the areas of the individual peaks (A2, A3, etc). At step 306, compares the T-wave area or areas against a baseline T-wave area (A1) previously obtained for the patient to calculate one or more numerical values indicative of ventricular dyssynchrony (such as $\Delta A$ or Asplit/Abase). That is, prior to the onset of heart failure, the pacer/ICD calculates the average area under the single T-wave peak of the IEGM of the patient. Preferably, the areas of the T-waves of numerous heartbeats are calculated and averaged to obtain the baseline area (A1). (The "baseline area" obtained prior to heart failure should not be confused with the "baseline voltage" used to calculate individual peak areas, which is evaluated on a beat-by-beat basis.) In some implementations, different baseline area values are calculated at different heart rates, since T-wave area can be affected by heart rate.

The comparison, performed at step 306, may depend on the number of peaks present within the T-waves. If only a single peak is present, then only a single area value is obtained (A2), which is compared against the baseline area (A1). For example, the difference A2–A1 may be calculated $\Delta A$. If $\Delta A$ is greater than 0.0, i.e. A2 is greater than A1, ventricular dyssynchrony is indicated. The larger the value of $\Delta A$, the more severe the dyssynchrony. In some implementations, $\Delta A$ is compared against a predetermined ventricular dyssynchrony threshold value that is set greater than 0.0, so that slight variations in A2 that arise naturally within the patient are not misinterpreted as being indicative of dyssynchrony. As noted, separate values for the baseline area (A1) can be calculated for different heart rates. If so, then the appropriate value of A1 is retrieved at step 306 from memory for comparison against the newly calculated value of A2, depending upon the heart rate at which A2 was obtained.

If the T-wave has bifurcated into two peaks, then the pacer/ICD preferably compares the area of individual peaks against the baseline area. That is, ΔA may be calculated based on A3−A1 or A2−A1, with one or both of these values compared against the ventricular dyssynchrony threshold. Alternatively, A2 and A3 can be summed then compared against A1. Or, separate values of ΔA may be calculated from A3 and A2, then averaged together, with the average value of ΔA then compared against a suitable ventricular dyssynchrony threshold. As can be appreciated, a variety of specific implementations can be used. Otherwise routine experimentation can be performed to identify optimal comparison algorithms for use with T-wave areas and to determine appropriate threshold values for use with particular patients. If the T-wave has fractionated into still more peaks, then still more individual area values can be calculated (i.e. A2, A3, A4, etc.) for comparison, alone or in combination, against baseline area A1.

Alternatively, rather than taking the difference of the newly calculated T-wave area (A2, A3, etc.) against A1, the pacer/ICD may instead calculate the ratio of the areas, i.e., A2/A1, A3/A1, etc. In any case, these ratio values are then compared against a predetermined ventricular dyssynchrony threshold value. Again, the comparison, performed at step 306, may depend on the number of peaks present within the T-waves. If only a single peak is present, then only a single ratio is obtained (A2/A1), which is compared against 1.0 or other suitable threshold values. That is, if A2/A1 is greater than 1.0 (or other threshold value), ventricular dyssynchrony is indicated. The larger the value of A2/A1, the more severe the dyssynchrony. Also, as noted, separate values for the baseline area (A1) can be calculated for different heart rates. The appropriate value of A1 is retrieved at step 306 from memory for use with the newly calculated value of A2, depending upon the heart rate at which A2 was obtained.

If the T-wave has bifurcated into two peaks, then the pacer/ICD preferably compares the area of individual peaks against the baseline area. That is, separate ratios may be calculated based on A3/A1 or A2/A1, with one or both of these ratios compared against the ventricular dyssynchrony threshold. Alternatively, A2 and A3 can be summed before the ratio with A1 is calculated. Or, separate ratios may be calculated from A3/A1 and A2/A1, then averaged together, with the average value of the ratio then compared against a suitable ventricular dyssynchrony threshold. As can be appreciated, a variety of specific ratio-based implementations can be used. If the T-wave has fractionated into still more peaks, then still more individual ratio values can be calculated (i.e. A2/A1, A3/A1, A4/A1, etc.) for comparison, alone or in combination, against a suitable threshold value indicative of ventricular dyssynchrony.

In any case, assuming the various area-based threshold comparisons are negative, then no ventricular dyssynchrony is indicated, at step 308. However, if the various area-based threshold comparisons are positive, then ventricular dyssynchrony is thereby detected, at step 310. (As with the preceding embodiment, ventricular dyssynchrony is preferably detected only if some minimum number of T-waves meet the detection criteria.) The pacer/ICD then, at step 312, evaluates the degree of dyssynchrony based on the various area differences or ratios. In general, the greater the difference between new T-wave area to baseline area (i.e. A2−A1) or the greater the ratio of new T-wave area to baseline area (i.e. A2/A1), the more severe the dyssynchrony. At step 314, the pacer/ICD tracks progression, if any, in heart failure based on changes in degree of ventricular dyssynchrony. As discussed above, within a patient known to have heart failure, the degree of ventricular dyssynchrony may be used as a proxy for the severity of heart failure. An increase in ventricular dyssynchrony is thereby deemed to be indicative of progression of heart failure. If the patient has not already been diagnosed with heart failure, the initial detection of ventricular dyssynchrony base on T-wave areas is indicative of possible heart failure. Accordingly, heart failure detection and evaluation techniques of the type cited above are preferably activated to determine if the patient indeed has heart failure. Diagnostic data is also stored and suitable warnings are issued at step 314 as well. At step 316, the pacer/ICD controls pacing to reduce the degree of dyssynchrony and to ameliorate heart failure by reducing area of peaks (or troughs) within T-waves relative to the baseline area, using adaptive techniques already described.

FIG. 7 provides exemplary IEGM signals, which particularly illustrate the area values exploited by the technique of FIG. 6. A first IEGM 318 is taken at baseline, i.e. it is the IEGM of a test subject without heart failure and without ventricular dyssynchrony. Each heartbeat of IEGM 318 has a T-wave with a single peak. The area of the T-wave calculated relative to a baseline voltage 320 is denoted by A1. A second IEGM 322 is taken from a test subject with ventricular dyssynchrony due to CHF. Each heartbeat of IEGM 322 has a T-wave with multiple peaks. The areas (A2, A3) of the peaks are calculated relative to a voltage baseline 324. As can be seen, in this example, each of the two areas is considerably greater than that of the baseline area. Hence, a numerical comparison of either of the areas against A1 yields an indication of ventricular dyssynchrony and triggers appropriate adaptive adjustments to pacing therapy.

Figure 8:
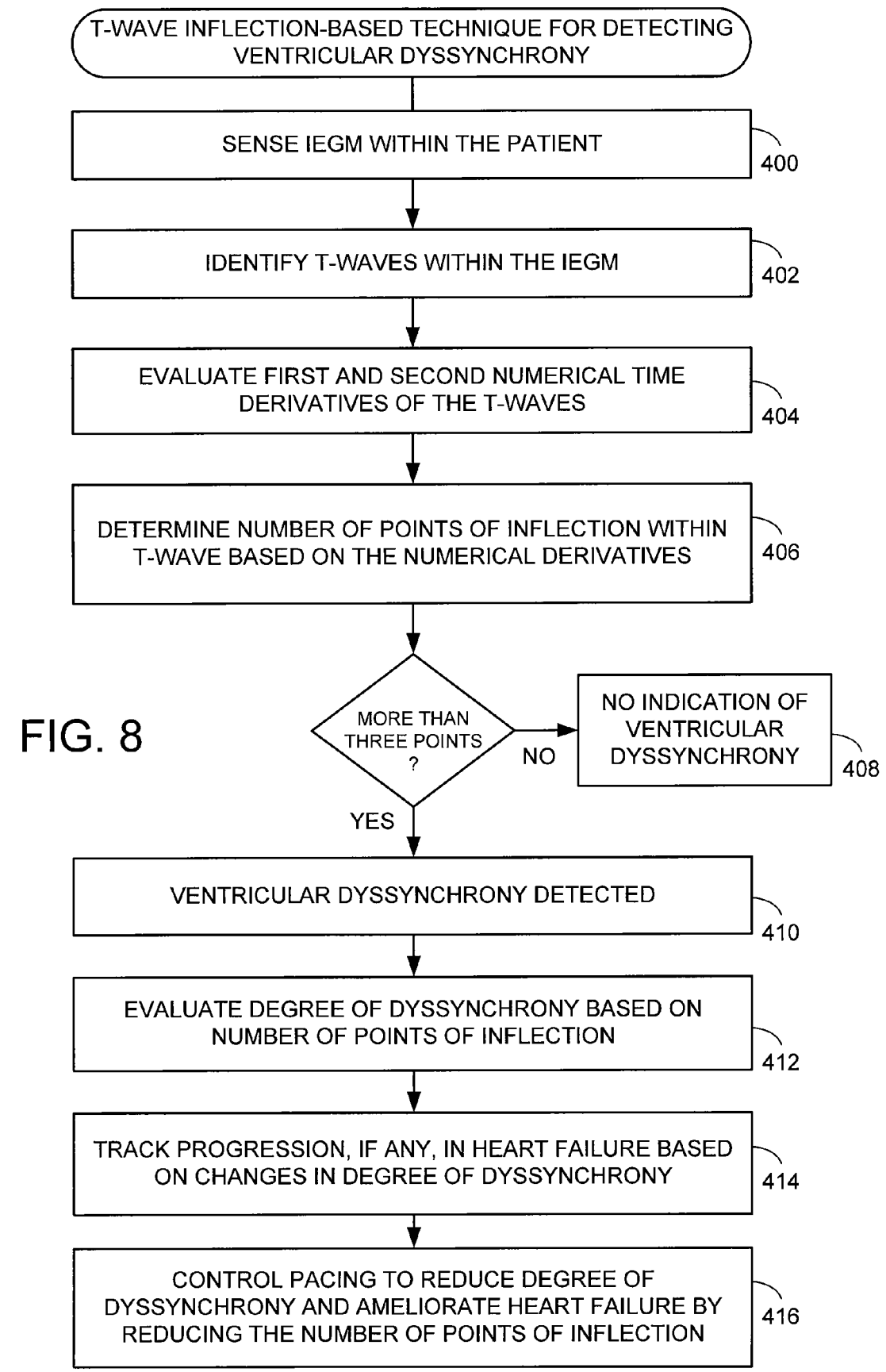
FIG. 8 illustrates a third illustrative embodiment of the general technique of FIG. 2 wherein T-wave points of inflection are exploited to detect ventricular dyssynchrony.
Figure 9:
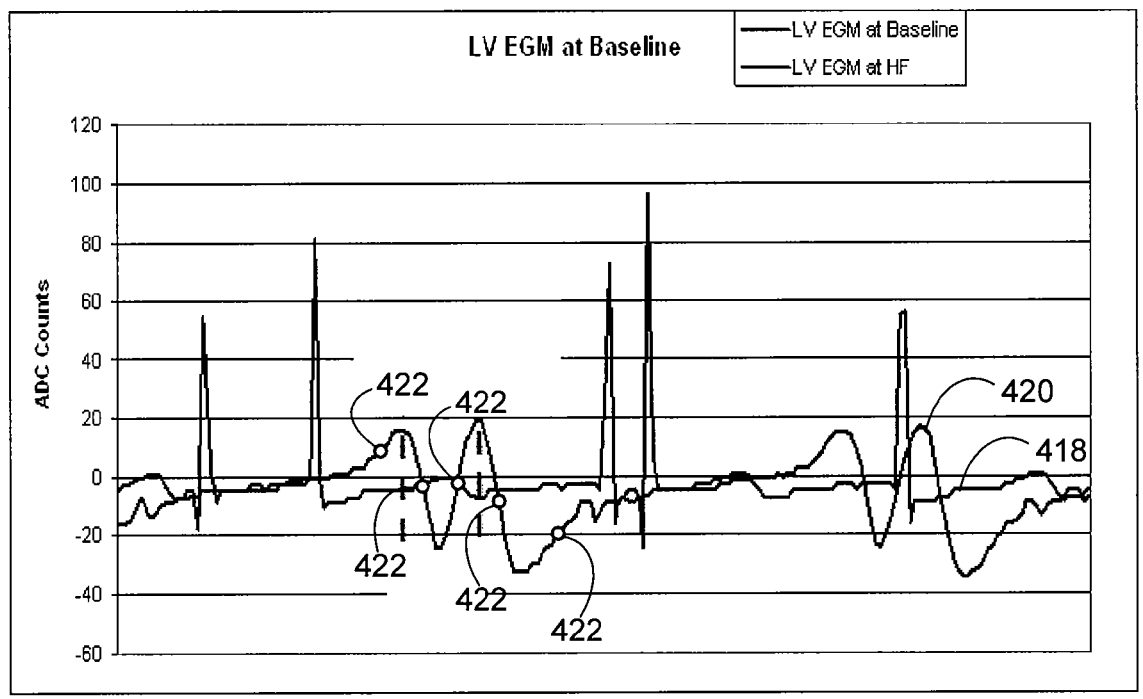
FIG. 9 provides an exemplary graph illustrating T-wave points of inflection, which may be exploited the method of FIG. 3 to detect and evaluate ventricular dyssynchrony.

FIGS. 8-9 illustrate inflection point-based techniques for evaluating ventricular dyssynchrony based on T-wave area. Beginning at step 400 of FIG. 8, the pacer/ICD senses the IEGM and, at step 402, identifies T-waves therein. At step 404, the pacer/ICD evaluates the first and second numerical derivatives of the IEGM signals within the T-waves, using otherwise conventional numerical techniques. At step 406, the pacer/ICD determines and counts the number of points of inflection within the T-wave based on the numerical derivatives. Generally, a point of inflection is the point where the curvature of a time-varying signal changes sign. This is also the point where the second derivative changes sign. Accordingly, the pacer/ICD may identify points of inflection by identifying points where the second derivative of the IEGM signals is zero. Given that noise is typically present within the IEGM, it may be appropriate to first filter the noise or preprocess the IEGM (e.g. fit curves or splines to the IEGM signal), then identify the points of inflection therefrom. Also, it is important to carefully detect the beginning and end points of the T-waves so that the first and last points of inflection within the T-wave can be properly detected. Techniques for identifying the beginning and end points of T-waves are discussed in the patent sited above. See, for example, the patent to McClure (U.S. Pat. No. 6,650,931), cited above.

If there are no more than three points of inflection within the T-wave, then no ventricular dyssynchrony is indicated, at step 408. However, if there are four or more points of inflection per T-wave, then ventricular dyssynchrony is thereby detected, at step 410. As in the preceding embodiments, ventricular dyssynchrony is preferably not detected based only on a single T-wave but is instead detected only if some minimum number of T-waves meet the detection criteria. The pacer/ICD then, at step 412, evaluates the degree of dyssynchrony based on number of points of inflection. Additionally, or alternatively, the time delay between first and last points of inflection can be measured and used as a basis of detecting ventricular dyssynchrony. At step 414, the pacer/ICD tracks progression, if any, in heart failure based on changes in degree of ventricular dyssynchrony determined from the points of inflection. At step 416, the pacer/ICD controls pacing to reduce the degree of dyssynchrony and to ameliorate heart failure by reducing number of points of inflection within T-waves and/or the time delay therebetween, using adaptive techniques already described.

FIG. 9 provides exemplary bipolar IEGM signals, which particularly illustrate the points of inflection exploited by the technique of FIG. 8. A first IEGM 418 is taken at baseline, i.e. without heart failure and without ventricular dyssynchrony. A second IEGM 420 is taken from a test subject with ventricular dyssynchrony due to CHF. Each T-wave of baseline IEGM 418 has three points of inflection—one between the starting point of the T-wave, another between the single peak and the single trough of the T-wave, and a third between the trough of the T-wave and the end point of the T-wave. These are not specifically identified in the figure so as not to obscure the points of inflection of the T-wave of IEGM 420. With bipolar IEGM 420, each T-wave has five points of inflection (generally denoted by reference numeral 422), which is indicative of ventricular dyssynchrony. As already explained, if CHF becomes even more severe, still greater fractionation of the T-wave can occur, yielding even more points of inflection. Accordingly, a count of the number of points of inflection is indicative of the degree of ventricular dyssynchrony.

Figure 10:
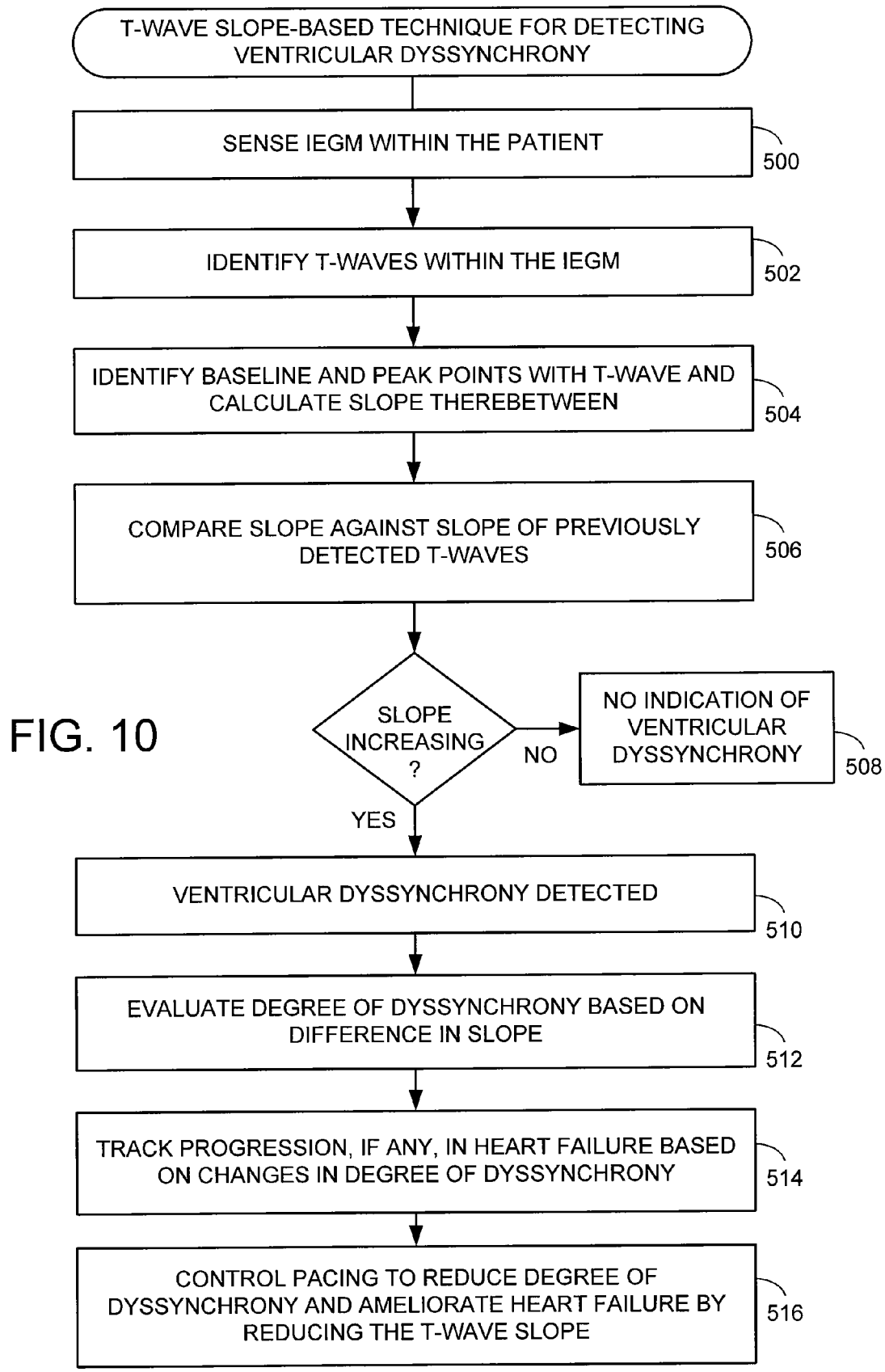
FIG. 10 illustrates a fourth illustrative embodiment of the general technique of FIG. 2 wherein T-wave slopes are exploited to detect ventricular dyssynchrony.
Figure 11:
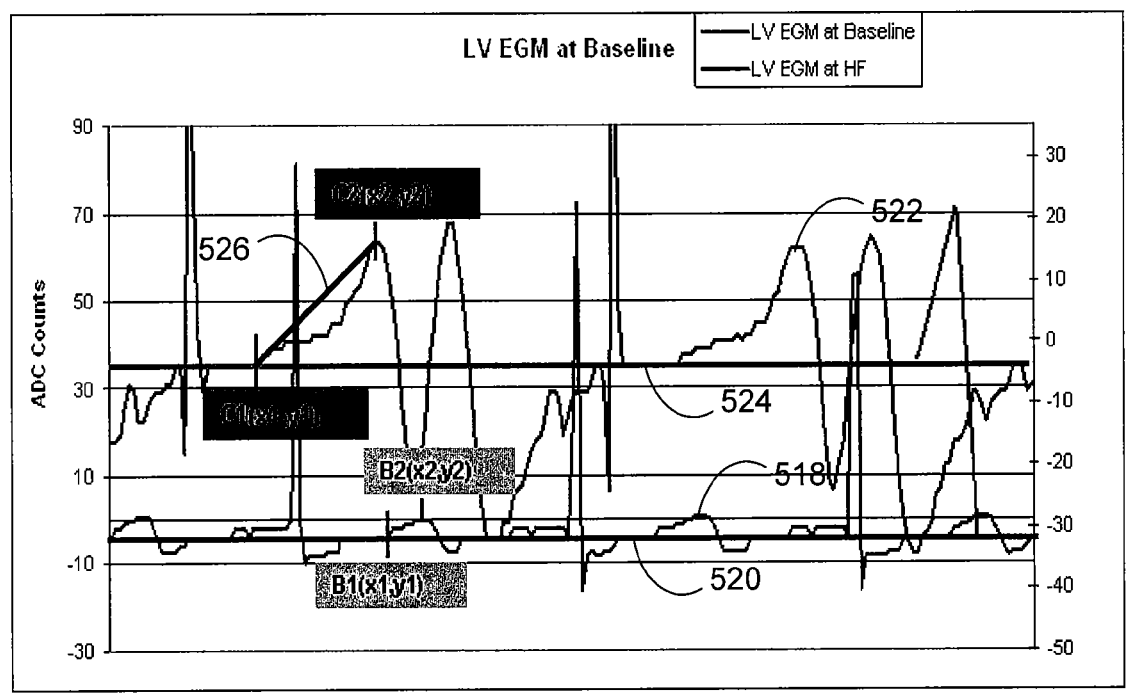
FIG. 11 provides an exemplary graph illustrating T-wave slopes, which may be exploited the method of FIG. 3 to detect and evaluate ventricular dyssynchrony.

FIGS. 10-11 illustrate slope-based techniques for evaluating ventricular dyssynchrony based on T-wave area. Beginning at step 500 of FIG. 10, the pacer/ICD senses the IEGM and, at step 502, identifies T-waves therein. At step 504, the pacer/ICD identifies baseline and peak points within the T-waves and calculates slopes therebetween. In one example, the baseline point of a T-wave is its starting point, as determined using otherwise conventional techniques. For example, the first point at which the IEGM signal exceeds a voltage baseline is deemed to be the starting point of the T-wave. The pacer/ICD then calculates an upslope value by detecting the time and voltage of the baseline point (C1 (x,y)) and the time and voltage of the first peak of the T-wave (C2 (x,y)), then calculates the upslope (dC/dt) of the newly detected T-wave using standard arithmetic. Additionally or alternatively, a downslope value may also be calculated at step 504 based on the last peak and the end point of the T-wave. At step 506, the pacer/ICD compares the T-wave slope values against baseline T-wave slope values (dB/dt) previously obtained for the patient to determine if the slope is increasing, i.e. the pacer/ICD calculates one or more numerical values indicative of ventricular dyssynchrony (such as $d\Delta/dt$, where $d\Delta/dt = dC/dt - dB/dt$). That is, prior to the onset of heart failure, the pacer/ICD calculates the upslope (and/or the downslope) of T-waves of the IEGM of the patient. Preferably, the upslopes (and/or downslopes) of the T-waves of numerous heartbeats are calculated and averaged to obtain the baseline slopes. (The "baseline slope" obtained prior to heart failure should not be confused with the "baseline point" used to calculate individual T-wave slopes, which is evaluated on a beat-by-beat basis.) In some implementations, different baseline slope values are calculated at different heart rates, since T-wave slope can be affected by heart rate.

In one example, $d\Delta/dt$ is calculated. If $d\Delta/dt$ is greater than 0.0, i.e. dC/dt is greater dB/dt, ventricular dyssynchrony is indicated. The larger the value of $d\Delta/dt$, the more severe the dyssynchrony. In some implementations, $d\Delta/dt$ is compared against a predetermined ventricular dyssynchrony threshold value that is set greater than 0.0, so that slight variations in $d\Delta/dt$ that arise naturally within the patient are not misinterpreted as being indicative of dyssynchrony. As noted, separate values for the baseline slope (dB/dt) can be calculated for different heart rates. The appropriate value of dB/dt is retrieved at step 506 for comparison against the newly calculated value of dC/dt, depending upon the heart rate at which dC/dt was obtained. If both upslope and downslope values are determined, then the pacer/ICD may compare the upslope to a baseline upslope and the downslope to a baseline downslope. Alternatively, rather than taking the difference of the newly calculated T-wave slopes against the baseline slope, the pacer/ICD may instead calculate the ratio of slopes, i.e., (dB/dt)/(dC/dt). These ratio values are then compared against a predetermined ventricular dyssynchrony threshold value. As can be appreciated, a variety of specific implementations can be used. Otherwise routine experimentation can be performed to identify optimal comparison algorithms for use with T-wave slopes and to determine appropriate threshold comparison values for use with particular patients.

In any case, assuming the various slope-based threshold comparisons are negative, then no ventricular dyssynchrony is indicated, at step 508. However, if the various slope-based threshold comparisons are positive, then ventricular dyssynchrony is thereby detected, at step 510. (As with the preceding embodiments, ventricular dyssynchrony is preferably detected only if some minimum number of T-waves meet the detection criteria.) The pacer/ICD then, at step 512, evaluates the degree of dyssynchrony based on the various slope differences or slope ratios. In general, the greater the difference between new T-wave slope to the baseline slope (i.e. dC/dt−dB/dt) or the greater the ratio of new T-wave slopes to baseline slopes (i.e. (dC/dt)/(dB/dt)), the more severe the dyssynchrony. At step 514, the pacer/ICD tracks progression, if any, in heart failure based on changes in degree of ventricular dyssynchrony. At step 516, the pacer/ICD controls pacing to reduce the degree of dyssynchrony and to ameliorate heart failure by reducing slope of the T-waves relative to the baseline slopes, using adaptive techniques already described.

FIG. 11 provides exemplary IEGM signals, which particularly illustrate the slope values exploited by the technique of FIG. 10. A first IEGM 518 is taken at baseline, i.e. it is the IEGM of a test subject without heart failure and without ventricular dyssynchrony. A baseline point B1 (x1, y1) is detected by determining the first point at which the IEGM voltage exceeds a voltage baseline 520. A peak point B2 (x2, y2) is then detected by identifying the first peak of the IEGM. A slope (not specifically illustrated) is calculated therebetween. A second IEGM 522 is representative of a test subject with ventricular dyssynchrony due to CHF. A first point C1 (x1, y1) is detected by determining the first point at which the IEGM voltage exceeds a voltage baseline 524. A peak point C2 (x2, y2) is then detected by identifying the first peak of the IEGM. An upslope 526 is calculated therebetween.

Figure 12:
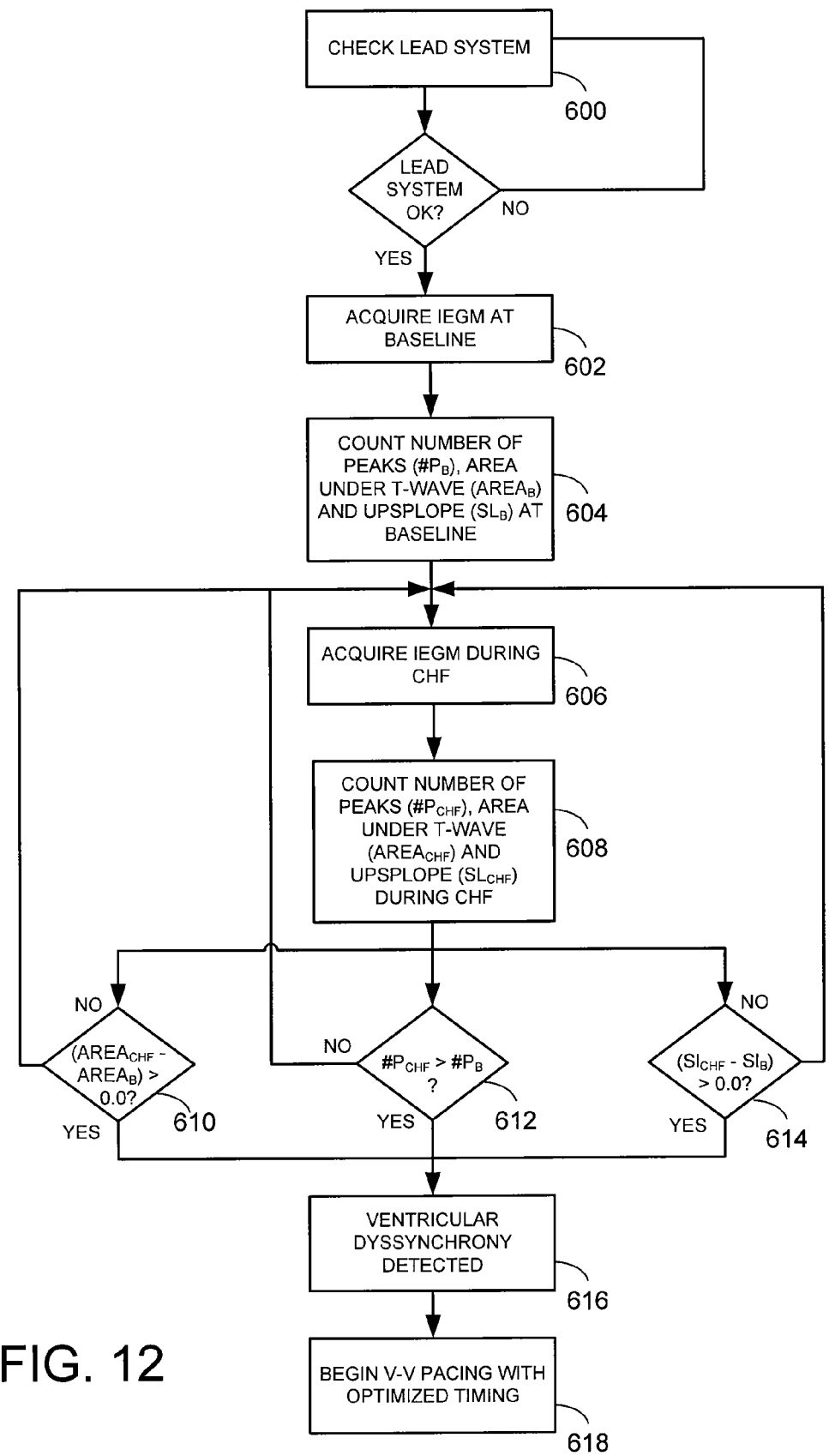
FIG. 12 illustrates an exemplary combined method for determining various T-wave parameters pertinent to ventricular dyssynchrony for use with the general technique of FIG. 2.

Turning now to FIG. 12, a combined technique is illustrated wherein multiple T-wave morphological parameters are evaluated at the same time. FIG. 12 also illustrates the manner by which baseline values are obtained for comparison against subsequent values detected after onset of CHF. Many of the individual steps have already been described and hence will not be described again in detail. Briefly, beginning at step 600, the pacer/ICD checks its lead system to verify that it is operating correctly. This may be performed, for example, by evaluating lead impedance. Assuming the lead system is okay, then at step 602, the pacer/ICD acquires a baseline IEGM, i.e. a pre-CHF baseline IEGM. This may be performed following initial device implant, assuming the patient is free of CHF at that time. If the patient already has heart failure, the pacer/ICD nevertheless detects baseline IEGM values so that progression (or regression) of CHF can be tracked. At step 604, the pacer/ICD counts the number of T-wave peaks (#PB), evaluates the area under T-wave ($AREA_B$) and calculated an upslope (SLB) value (or downslope value) at baseline. These values are stored in memory.

Then, during subsequent use, the pacer/ICD acquired new IEGM signals, at step 606, and at step 608, then counts the number of T-wave peaks ($\#P_{CHF}$), evaluates the area under T-wave ($AREA_{CHF}$) and calculated an upslope ($SL_{CHF}$) value (or downslope value). These values are referred to in FIG. 12 as "CHF" values, thought though it should be understood that it is not yet known whether CHF has indeed developed within the patient. At steps 610, 612 and 614, the pacer/ICD performs various comparisons using the just detected T-wave values and the previously stored baseline values. If each of the comparisons is indicative of ventricular dyssynchrony, then ventricular dyssynchrony is thereby detected, at step 616, and appropriate warning signals are preferably generated to alert the patient's physician so he or she can determine if the patient now suffers from heart failure or if the dyssynchrony arose from another cause. At step 618, the pacer/ICD begins biventricular (i.e. V-V) pacing with adaptively optimized timing, determined using the techniques discussed above. In other implementations, points of inflection are additionally or alternatively evaluated or timing delays between T-waves peaks are exploited, as already described. As can be appreciated a wide rage of alternatives are consistent with the principles of the invention. For example, morphological aspects, such as those described above, of T-waves from one ventricle can be compared to morphologies of the other ventricle. A significant difference between the two morphological aspects can be indicative of progressive interventricular dyssynchrony and heart failure. Therapy provided by CRT device would aim at reducing morphological and temporal differences associated with the two ventricles.

In some examples, the above-described T-wave parameters are measured and compared only while the patient is at rest for consistency. A sleep or circadian detector may be used to identify appropriate periods of time to measure the values. Any of a variety of otherwise conventional sleep detection techniques may be employed. Examples are set forth in the following patents or patent applications: U.S. Pat. No. 5,476,483, to Bornzin et al., entitled "System and Method for Modulating the Base Rate During Sleep for a Rate-responsive Cardiac Pacemaker"; U.S. Pat. No. 6,128,534 to Park et al., entitled "Implantable Cardiac Stimulation Device And Method For Varying Pacing Parameters To Mimic Circadian Cycles"; and in U.S. patent application Ser. No. 10,339,989 of Koh et al., entitled "System And Method For Detecting Circadian States Using An Implantable Medical Device", filed Jan. 10, 2003. In addition, posture detectors may be used to determine when the patient is in a certain predetermined posture (such as supine) so as to reduce or eliminate any variations in the measurement of the T-wave values that may be due to changes in posture. See, e.g., posture detection techniques described in U.S. Pat. No. 6,658,292 of Kroll et al., entitled "Detection of Patient's Position and Activity Status Using 3D Accelerometer-Based Position Sensor". See, also, U.S. patent application Ser. No. 10/329,233, of Koh et al., entitled "System and Method for Determining Patient Posture Based On 3-D Trajectory Using an Implantable Medical Device," filed Dec. 23, 2002.

What have been described are various techniques for detecting ventricular dyssynchrony based on T-wave morphological parameters and for controlling therapy in response thereto. For the sake of completeness, a detailed description of an exemplary pacer/ICD for controlling these functions will now be provided. However, principles of invention may be implemented within other pacer/ICD implementations or within other implantable devices. Furthermore, although examples described herein involve processing of the various signals by the implanted device itself, some operation may be performed using an external device. For example, recorded IEGM data may be transmitted to an external device, which processes the data to evaluate ventricular dyssynchrony. Processing by the implanted device itself is preferred as that allows prompt changes to pacing control parameters so as to address any progression in ventricular dyssynchrony.

Exemplary Pacemaker/ICD

FIG. 13 provides a simplified block diagram of the pacer/ICD, which is a multi-chamber stimulation device capable of treating both fast and slow arrhythmias with stimulation therapy, including cardioversion, defibrillation, and pacing stimulation, as well as being capable of performing the functions discussed above. To provide atrial chamber pacing stimulation and sensing, pacer/ICD 10 is shown in electrical communication with a heart 712 by way of a left atrial lead 720 having an atrial tip electrode 722 and an atrial ring electrode 723 implanted in the atrial appendage. Pacer/ICD 10 is also in electrical communication with the heart by way of a right ventricular lead 730 having, in this embodiment, a ventricular tip electrode 732, a right ventricular ring electrode 734, a right ventricular (RV) coil electrode 736, and a superior vena cava (SVC) coil electrode 738. Typically, the right ventricular lead 718 is transvenously inserted into the heart to place the RV coil electrode 736 in the right ventricular apex, and the SVC coil electrode 738 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a CS lead 724 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 724 is designed to receive atrial and ventricular cardiac signals and to deliver left ventricular pacing therapy using at least a left ventricular RING electrode 725, a left ventricular tip electrode 726, and to deliver left atrial pacing therapy using at least a left atrial ring electrode 727, and shocking therapy using at least a left atrial coil electrode 728. With this configuration, biventricular pacing can be performed. Although only three leads are shown in FIG. 12, it should also be understood that additional stimulation leads (with one or more pacing, sensing and/or shocking electrodes) might be used in order to efficiently and effectively provide pacing stimulation to the left side of the heart or atrial cardioversion and/or defibrillation.

Figure 14:
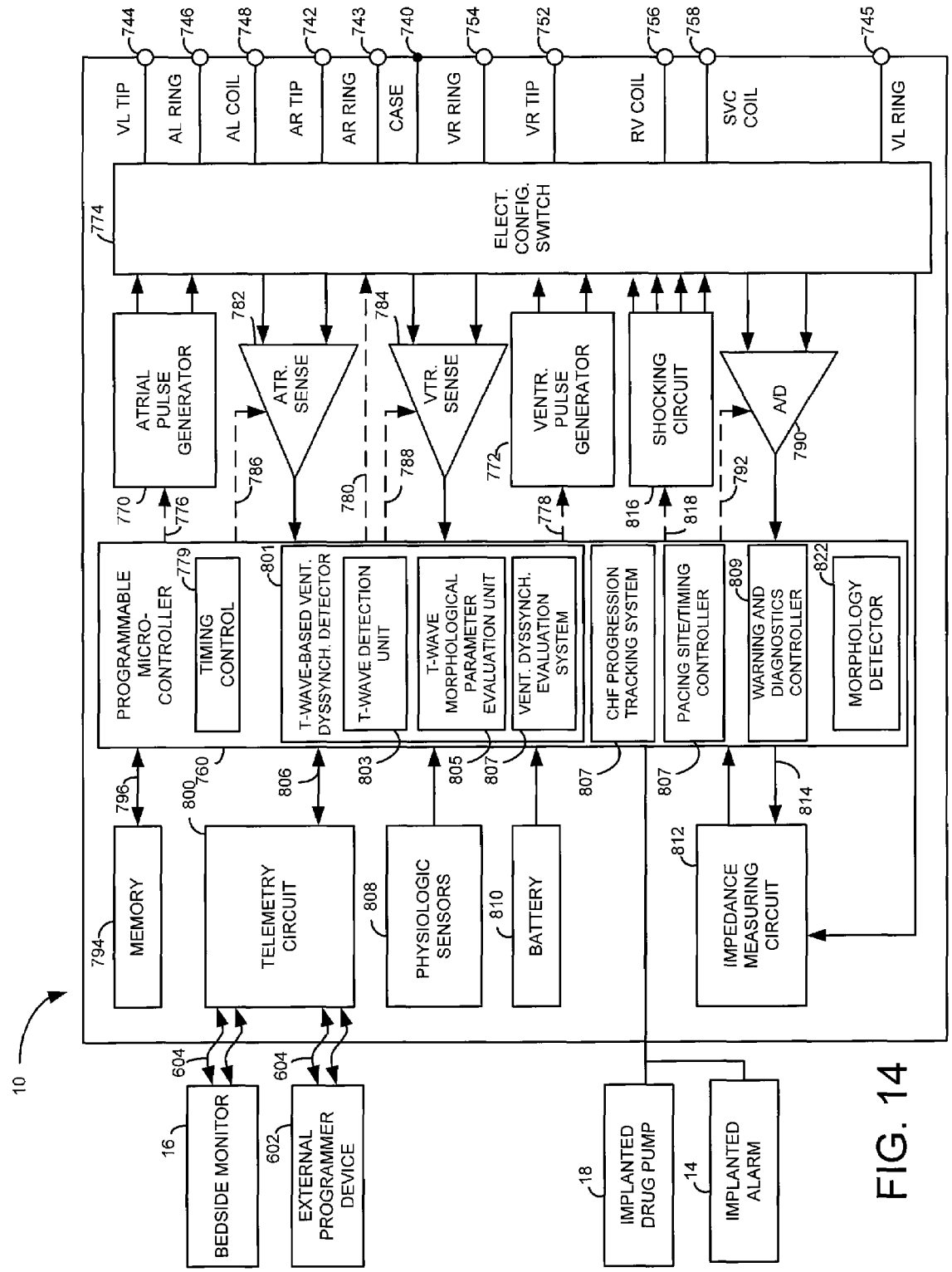
FIG. 14 is a functional block diagram of the pacer/ICD of FIG. 13, illustrating basic circuit elements that provide cardioversion, defibrillation and/or pacing stimulation in four chambers of the heart and particularly illustrating components for evaluating ventricular dyssynchrony based on T-waves and for controlling therapy in response thereto.

A simplified block diagram of internal components of pacer/ICD 10 is shown in FIG. 14. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 740 for pacer/ICD 10, shown schematically in FIG. 14, is often referred to as the "can", "case" or "case electrode" and may be programmably selected to act as the return electrode for all "unipolar" modes. The housing 740 may further be used as a return electrode alone or in combination with one or more of the coil electrodes, 728, 736 and 738, for shocking purposes. The housing 740 further includes a connector (not shown) having a plurality of terminals, 742, 743, 744, 745 746, 748, 752, 754, 756 and 758 (shown schematically and, for convenience, the names of the electrodes to which they are connected are shown next to the terminals). As such, to achieve right atrial sensing and pacing, the connector includes at least a right atrial tip terminal ($A_R$ TIP) 742 adapted for connection to the atrial tip electrode 722 and a right atrial ring ($A_R$ RING) electrode 743 adapted for connection to right atrial ring electrode 723. To achieve left chamber sensing, pacing and shocking, the connector includes at least a left ventricular ring terminal ($V_L$ RING) 745, a left ventricular tip terminal ($V_L$ TIP) 744, a left atrial ring terminal ($A_L$ RING) 746, and a left atrial shocking terminal ($A_L$ COIL) 748, which are adapted for connection to the left ventricular ring electrode 726, the left atrial ring electrode 727, and the left atrial coil electrode 728, respectively. To support right chamber sensing, pacing and shocking, the connector further includes a right ventricular tip terminal ($V_R$ TIP) 752, a right ventricular ring terminal ($V_R$ RING) 754, a right ventricular shocking terminal ($V_R$ COIL) 756, and an SVC shocking terminal (SVC COIL) 758, which are adapted for connection to the right ventricular tip electrode 732, right ventricular ring electrode 734, the $V_R$ coil electrode 736, and the SVC coil electrode 738, respectively.

At the core of pacer/ICD 10 is microcontroller 104, which controls the various modes of stimulation therapy. As is well known in the art, the microcontroller 104 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 104 includes the ability to process or monitor input signals (data) as controlled by a program code stored in a designated block of memory. The details of the design and operation of the microcontroller 104 are not critical to the invention. Rather, any suitable microcontroller 104 may be used that carries out the functions described herein. The use of microprocessor-based control circuits for performing timing and data analysis functions are well known in the art.

As shown in FIG. 14, an atrial pulse generator 770 and a ventricular pulse generator 772 generate pacing stimulation pulses for delivery by the right atrial lead 720, the right ventricular lead 718, and/or the CS lead 724 via an electrode configuration switch 774. It is understood that in order to provide stimulation therapy in each of the four chambers of the heart, the atrial and ventricular pulse generators, 770 and 772, may include dedicated, independent pulse generators, multiplexed pulse generators or shared pulse generators. The pulse generators, 770 and 772, are controlled by the microcontroller 104 via appropriate control signals, 776 and 778, respectively, to trigger or inhibit the stimulation pulses.

The microcontroller 104 further includes timing control circuitry (not separately shown) used to control the timing of such stimulation pulses (e.g., pacing rate, atrioventricular delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 774 includes a plurality of switches for connecting the desired electrodes to the appropriate I/O circuits, thereby providing complete electrode programmability. Accordingly, the switch 774, in response to a control signal 780 from the microcontroller 104, determines the polarity of the stimulation pulses (e.g., unipolar, bipolar, combipolar, etc.) by selectively closing the appropriate combination of switches (not shown) as is known in the art.

Atrial sensing circuits 782 and ventricular sensing circuits 784 may also be selectively coupled to the right atrial lead 720, CS lead 724, and the right ventricular lead 718, through the switch 774 for detecting the presence of cardiac activity in each of the four chambers of the heart. Accordingly, the atrial (ATR. SENSE) and ventricular (VTR. SENSE) sensing circuits, 782 and 784, may include dedicated sense amplifiers, multiplexed amplifiers or shared amplifiers. The switch 774 determines the "sensing polarity" of the cardiac signal by selectively closing the appropriate switches, as is also known in the art. In this way, the clinician may program the sensing polarity independent of the stimulation polarity. Each sensing circuit, 782 and 784, preferably employs one or more low power, precision amplifiers with programmable gain and/or automatic gain control and/or automatic sensitivity control, bandpass filtering, and a threshold detection circuit, as known in the art, to selectively sense the cardiac signal of interest. The automatic gain control and/or automatic sensitivity control enables pacer/ICD 10 to deal effectively with the difficult problem of sensing the low amplitude signal characteristics of atrial or ventricular fibrillation. The outputs of the atrial and ventricular sense amplifiers may be in the form of interrupts. The microcontroller 104 triggers or inhibits the atrial and ventricular pulse generators, 770 and 772, respectively, in a demand fashion in response to the absence or presence of cardiac activity in the appropriate chambers of the heart, as represented by the atrial and ventricular event interrupts.

For arrhythmia detection, pacer/ICD 10 utilizes the atrial and ventricular sensing circuits, 782 and 784, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 104 by comparing them to a predefined rate zone limit (i.e., bradycardia, normal, atrial tachycardia, atrial fibrillation, low rate ventricular tachycardia, high rate ventricular tachycardia, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 790. The data acquisition system 790 is configured to acquire intracardiac electrogram signals, convert the raw analog data into a digital signal, and store the digital signals for later processing and/or telemetric transmission to an external device 802. The data acquisition system 790 is coupled to the right atrial lead 720, the CS lead 724, and the right ventricular lead 718 through the switch 774 to sample cardiac signals across any pair of desired electrodes. The microcontroller 104 is further coupled to a memory 794 by a suitable data/address bus 796, wherein the programmable operating parameters used by the microcontroller 104 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 794 through a telemetry circuit 800 in telemetric communication with the external device 802, such as a programmer, transtelephonic transceiver or a diagnostic system analyzer. The telemetry circuit 800 is activated by the microcontroller by a control signal 806. The telemetry circuit 800 advantageously allows intracardiac electrograms and status information relating to the operation of pacer/ICD 10 (as contained in the microcontroller 104 or memory 794) to be sent to the external device 802 through an established communication link 804. Pacer/ICD 10 further includes an accelerometer or other physiologic sensor 808, commonly referred to as a "rate-responsive" sensor because it is typically used to adjust pacing stimulation rate according to the exercise state of the patient. However, the physiological sensor 808 may further be used to detect changes in cardiac output, changes in the physiological condition of the heart, or diurnal changes in activity (e.g., detecting sleep and wake states) and to detect arousal from sleep. Accordingly, the microcontroller 104 responds by adjusting the various pacing parameters (such as rate, AV delay, V-V delay, etc.) at which the atrial and ventricular pulse generators, 770 and 772, generate stimulation pulses. While shown as being included within pacer/ICD 10, it is to be understood that the physiologic sensor 808 may also be external to pacer/ICD 10, yet still be implanted within or carried by the patient. A common type of rate responsive sensor is an activity sensor incorporating an accelerometer or a piezoelectric crystal, which is mounted within the housing 740 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 810, which provides operating power to all of the circuits shown in FIG. 14. The battery 810 may vary depending on the capabilities of pacer/ICD 10. If the system only provides low-voltage therapy, a lithium iodine or lithium copper fluoride cell may be utilized. For pacer/ICD 10, which employs shocking therapy, the battery 810 must be capable of operating at low current drains for long periods, and then be capable of providing high-current pulses (for capacitor charging) when the patient requires a shock pulse. The battery 810 should also have a predictable discharge characteristic so that elective replacement time can be detected. Accordingly, pacer/ICD 10 is preferably capable of high-voltage therapy and appropriate batteries.

As further shown in FIG. 14, pacer/ICD 10 is shown as having an impedance measuring circuit 812 which is enabled by the microcontroller 104 via a control signal 814. Impedance values may also be used for tracking respiration; for surveillance during the acute and chronic phases for proper lead positioning or dislodgement; for measuring respiration or minute ventilation; for measuring thoracic impedance for use in setting shock thresholds; for detecting when the device has been implanted; and for detecting the opening of heart valves, etc. The impedance measuring circuit 120 is advantageously coupled to the switch 74 so that any desired combination of electrodes may be used.

In the case where pacer/ICD 10 is intended to operate as an ICD, it detects the occurrence of an arrhythmia, and automatically applies an appropriate electrical shock therapy to the heart aimed at terminating the detected arrhythmia. To this end, the microcontroller 104 further controls a shocking circuit 816 by way of a control signal 818. The shocking circuit 816 generates shocking pulses of low (up to 0.5 joules), moderate (0.5-10 joules) or high energy (11 to 70 joules or more), as controlled by the microcontroller 104. Such shocking pulses are applied to the heart of the patient through at least two shocking electrodes, and as shown in this embodiment, selected from the left atrial coil electrode 728, the RV coil electrode 736, and/or the SVC coil electrode 738. The housing 740 may act as an active electrode in combination with the RV electrode 736, or as part of a split electrical vector using the SVC coil electrode 738 or the left atrial coil electrode 728 (i.e., using the RV electrode as a common electrode). Cardioversion shocks are generally considered to be of low to moderate energy level (so as to minimize pain felt by the patient), and/or synchronized with a VF event and/or pertaining to the treatment of tachycardia. Defibrillation shocks are generally of moderate to high energy level (i.e., corresponding to thresholds in the range of 8-40 joules), delivered asynchronously (since VF events may be too disorganized), and pertaining exclusively to the treatment of fibrillation. Accordingly, the microcontroller 104 is capable of controlling the synchronous or asynchronous delivery of the shocking pulses.

Microcontroller 60 also includes various components for controlling the various operations described above with reference to FIGS. 1-12. In particular, the microcontroller includes a T-wave-based ventricular dyssynchrony detector 801 operative to detect and evaluate ventricular dyssynchrony within the patient based, at least in part, on T-wave morphology. The ventricular dyssynchrony detector includes a T-wave detection unit 803 operative to identify a ventricular repolarization event within the electrical cardiac signal, a T-wave morphological feature evaluation unit 805 operative to evaluate at least one morphological feature of the repolarization event, and a T-wave-based ventricular dyssynchrony evaluation system 807 operative to detect and evaluate ventricular dyssynchrony within the patient based on morphological features of the repolarization events. Additionally, the microcontroller includes a CHF progression tracking unit operative to detect and track progression of heart failure in the patient based on the degree of ventricular dyssynchrony within the patient. A pacing site/timing controller 807 is operative to control the timing of pacing pulses delivered to the patient based on the degree of ventricular dyssynchrony or on the severity of heart failure. Controller 807, in some implementations, is also equipped to select and control the locations at which pacing pulses are delivered based, in part, on the degree of ventricular dyssynchrony or on the severity of heart failure, i.e. the controller specifies particular combinations of electrodes for use in delivering CRT pulses. The microcontroller also includes a warning and diagnostic controller 809 operative to control generating of warning signals as well as to control recording of appropriate diagnostic information within memory 794 pertinent to ventricular dyssynchrony and heart failure.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

The principles of the invention may be exploiting using other implantable systems or in accordance with other techniques. Thus, while the invention has been described with reference to particular exemplary embodiments, modifications can be made thereto without departing from scope of the invention. The various functional components of the exemplary systems described herein may be implemented using any appropriate technology including, for example, microprocessors running software programs or ASICs executing hard-wired logic operations. Note also that the term "including" as used herein is intended to be inclusive, i.e. "including but not limited to".

What is claimed is:

1. A method for use with an implantable medical device for detecting ventricular dyssynchrony, the method comprising:
   sensing an electrical cardiac signal within the patient in which the device is implanted;
   identifying a ventricular repolarization event within the electrical cardiac signal;
   evaluating a morphological feature of the repolarization event that is affected by ventricular dyssynchrony;
   detecting ventricular dyssynchrony within the patient based on the morphological feature of the repolarization event, wherein detecting ventricular dyssynchrony within the patient includes detecting ventricular dyssynchrony based on the presence of two or more peaks within an individual repolarization event; and
   evaluating a degree of severity of ventricular dyssynchrony within the patient based on the number of peaks within individual repolarization events.

2. The method of claim 1 wherein:
   sensing an electrical cardiac signal within the patient includes sensing an intracardiac electrogram (IEGM);
   identifying the ventricular repolarization event within the electrical cardiac signal includes identifying one or more T-waves within the IEGM; and
   detecting ventricular dyssynchrony within the patient includes detecting ventricular dyssynchrony based on the presence of two or more peaks within an individual T-wave.

3. The method of claim 1 wherein evaluating a degree of severity of ventricular dyssynchrony within the patient includes:
   counting the number of peaks within individual repolarization events; and
   associating a greater number of peaks as being indicative of a greater severity of ventricular dyssynchrony.

4. The method of claim 1 further including adjusting pacing timing parameters to reduce the number of peaks within individual repolarization events.

5. The method of claim 1 wherein evaluating the degree of severity of ventricular dyssynchrony within the patient includes:
   determining a time delay between peaks within individual repolarization events; and
   associating a greater time delay as being indicative of a greater severity of ventricular dyssynchrony.

6. The method of claim 5 wherein the time delay is determined between peaks observed within an individual repolarization event within an individual cardiac signal; and
   wherein the corresponding ventricular dyssynchrony is an intraventricular dyssynchrony.

7. The method of claim 6 wherein the individual cardiac signal is a left ventricular IEGM.

8. The method of claim 6 wherein the individual cardiac signal is a right ventricular IEGM.

9. The method of claim 5 wherein the time delay is determined between peaks observed within separate cardiac signals; and
   wherein the corresponding ventricular dyssynchrony is an interventricular dyssynchrony.

10. The method of claim 9 wherein the separate cardiac signals include a left ventricular IEGM and a right ventricular IEGM.

11. The method of claim 5 further including adjusting pacing timing parameters to reduce the time delay between peaks within individual repolarization events.

12. A method for use with an implantable medical device for detecting ventricular dyssynchrony, the method comprising:
   sensing an electrical cardiac signal within the patient in which the device is implanted;
   identifying a ventricular repolarization event within the electrical cardiac signal;
   evaluating a morphological feature of the repolarization event that is affected by ventricular dyssynchrony, wherein evaluating a morphological feature of the repolarization event includes evaluating an area associated with the repolarization event;
   detecting ventricular dyssynchrony within the patient based on the morphological feature of the repolarization event, wherein detecting ventricular dyssynchrony within the patient based on the morphological feature of the repolarization event includes:
      evaluating a numerical area associated with at least a portion of an individual repolarization event curve relative to an isoelectric line;
      comparing the area against a baseline area indicative of a lack of ventricular dyssynchrony; and
      associating a larger amount of area relative to the baseline area as being indicative of ventricular dyssynchrony; and
   evaluating the degree of severity of ventricular dyssynchrony within the patient based on the area.

13. The method of claim 12 wherein:
   sensing an electrical cardiac signal within the patient includes sensing an intracardiac electrogram (IEGM);
   identifying the ventricular repolarization event within the electrical cardiac signal includes identifying one or more T-waves within the IEGM; and
   detecting ventricular dyssynchrony within the patient based on the morphological feature of the repolarization event includes:
      evaluating a numerical area associated with at least a portion of the T-wave relative to an isoelectric line;
      comparing the area against a baseline area indicative of a lack of ventricular dyssynchrony; and
      associating a larger amount of area relative to the baseline area as being indicative of ventricular dyssynchrony.

14. The method of claim 12 wherein evaluating the degree of severity of ventricular dyssynchrony within the patient includes:
determining a difference between the area calculated for the repolarization event and the baseline area; and
associating a greater difference as being indicative of a greater severity of ventricular dyssynchrony.

15. The method of claim 14 further including adjusting pacing timing parameters to reduce the difference.

16. The method of claim 14 wherein evaluating the degree of severity of ventricular dyssynchrony within the patient includes:
determining a ratio of the area calculated for the repolarization event compared against the baseline area; and
associating a greater ratio as being indicative of a greater severity of ventricular dyssynchrony.

17. The method of claim 16 further including adjusting pacing timing parameters to reduce the ratio.

18. The method of claim 12 wherein evaluating the numerical area is performed to separately evaluate the areas associated with separate peaks of the repolarization event curve.

19. A method for use with an implantable medical device for detecting ventricular dyssynchrony, the method comprising:
sensing an electrical cardiac signal within the patient in which the device is implanted;
identifying a ventricular repolarization event within the electrical cardiac signal;
evaluating a morphological feature of the repolarization event that is affected by ventricular dyssynchrony, wherein evaluating a morphological feature of the repolarization event includes evaluating points of inflection associated with the repolarization event; and
detecting ventricular dyssynchrony within the patient based on the morphological feature of the repolarization event.

20. The method of claim 19 wherein:
sensing an electrical cardiac signal within the patient includes sensing an intracardiac electrogram (IEGM);
identifying the ventricular repolarization event within the electrical cardiac signal includes identifying one or more T-waves within the IEGM;
evaluating a morphological feature of the repolarization event includes evaluating points of inflection associated with the T-wave; and
detecting ventricular dyssynchrony within the patient based on the morphological feature of the repolarization event includes detecting ventricular dyssynchrony within the patient based on the detection of more than three points of inflection within an individual T-wave.

21. The method of claim 19 wherein detecting ventricular dyssynchrony within the patient based on the morphological feature of the repolarization event includes:
evaluating numerical derivatives of a repolarization event curve;
identifying points of inflexion within the repolarization event curve based on the numerical derivatives; and
associating more than three points of inflection within a single repolarization event as being indicative of ventricular dyssynchrony.

22. The method of claim 21 further including evaluating a degree of severity of ventricular dyssynchrony within the patient based on the points of inflection.

23. The method of claim 22 further including adjusting pacing timing parameters to reduce the degree of severity of ventricular dyssynchrony within the patient by reducing the number of points of inflection.

24. The method of claim 22 wherein evaluating a degree of severity of ventricular dyssynchrony within the patient includes
determining a total number of points of inflection within a individual repolarization event; and
associating a greater number of points of inflection as being indicative of a greater severity of ventricular dyssynchrony.

25. A method for use with an implantable medical device for detecting ventricular dyssynchrony, the method comprising:
sensing an electrical cardiac signal within the patient in which the device is implanted;
identifying a ventricular repolarization event within the electrical cardiac signal;
evaluating a morphological feature of the repolarization event that is affected by ventricular dyssynchrony, wherein evaluating a morphological feature of the repolarization event includes evaluating one or more slope values associated with the repolarization event;
detecting ventricular dyssynchrony within the patient based on the morphological feature of the repolarization event; and
adjusting pacing timing parameters to reduce the magnitude of the slope of individual repolarization event curves.

26. The method of claim 25 wherein:
sensing an electrical cardiac signal within the patient includes sensing an intracardiac electrogram (IEGM);
identifying the ventricular repolarization event within the electrical cardiac signal includes identifying one or more T-waves within the IEGM;
evaluating a morphological feature of the repolarization event includes evaluating one or more slope values associated with the T-wave;
detecting ventricular dyssynchrony within the patient based on the morphological feature of the repolarization event includes:
evaluating an upslope of the T-wave;
comparing the upslope against a baseline upslope indicative of a lack of ventricular dyssynchrony; and
associating a significant increase in the slope relative to the baseline slope as being indicative of ventricular dyssynchrony; and
adjusting pacing timing parameters includes adjusting pacing timing parameters to reduce the magnitude of the slope of T-waves.

27. The method of claim 25 wherein detecting ventricular dyssynchrony within the patient based on the morphological feature of the repolarization event includes:
evaluating a slope of a repolarization event curve;
comparing the slope against a baseline slope indicative of a lack of ventricular dyssynchrony;
associating a larger magnitude slope relative to the baseline slope as being indicative of ventricular dyssynchrony.

28. The method of claim 25 wherein the slope values include one or more of upslope values and downslope values.

29. The method of claim 25 further including evaluating a degree of severity of ventricular dyssynchrony within the patient based on the slope.

30. A method for use with an implantable medical device for detecting ventricular dyssynchrony, the method comprising:

sensing an electrical cardiac signal within the patient in which the device is implanted;
identifying a ventricular repolarization event within the electrical cardiac signal;
measuring a morphological feature of the repolarization event that is affected by ventricular dyssynchrony;
detecting ventricular dyssynchrony within the patient based on the morphological feature of the repolarization event;
evaluating a degree of severity of ventricular dyssynchrony within the patient based on the morphological feature of the repolarization event; and
evaluating progression of heart failure based on changes in the severity of ventricular dyssynchrony within the patient over time.

31. The method of claim 30 wherein:
sensing an electrical cardiac signal within the patient includes sensing an intracardiac electrogram (IEGM); and
identifying the ventricular repolarization event within the electrical cardiac signal includes identifying one or more T-waves within the IEGM.

32. A method for use with an implantable medical device for detecting ventricular dyssynchrony, the method comprising:
sensing an electrical cardiac signal within the patient in which the device is implanted;
identifying a ventricular repolarization event within the electrical cardiac signal;
measuring a plurality of morphological features of the repolarization event that is affected by ventricular dyssynchrony; and
detecting ventricular dyssynchrony within the patient based on the plurality of morphological features of the repolarization event.

33. The method of claim 32 wherein:
sensing an electrical cardiac signal within the patient includes sensing an intracardiac electrogram (IEGM); and
identifying the ventricular repolarization event within the electrical cardiac signal includes identifying one or more T-waves within the IEGM.

34. The method of claim 33 wherein the plurality of morphological features is selected from the group consisting of a number of peaks of an individual T-wave, an area under one or more peaks of an individual T-wave, a number of inflection points within an individual T-wave, a slope of an individual T-wave, and combinations thereof.

35. The method of claim 33 wherein the plurality of morphological features includes the number of peaks under an individual T-wave, the area under the individual T-wave, and the slope of the individual T-wave, and wherein detecting ventricular dyssynchrony within the patient based on the plurality of morphological features of the repolarization event includes:
comparing the number of peaks under an individual T-wave to a baseline value;
comparing the area under the individual T-wave to a baseline value;
comparing the slope of the individual T-wave to a baseline value; and
detecting ventricular dyssynchrony if each of said comparisons is indicative of ventricular dyssynchrony.

36. The method of claim 33 further including adaptively adjusting pacing timing parameters to reduce fractionation of T-waves or reduce the time delay between peaks of a T-wave.

37. The method of claim 34 further including adaptively adjusting pacing timing parameters to reduce ventricular dyssynchrony by adjusting an interventricular pacing delay.

38. The method of claim 34 further including adaptively adjusting pacing timing parameters to reduce ventricular dyssynchrony by adjusting a delay between a paced or sensed atrial event and a paced ventricular event.

39. A method for use with an implantable medical device for detecting ventricular dyssynchrony, the method comprising:
sensing an electrical cardiac signal within the patient in which the device is implanted;
identifying a ventricular repolarization event within the electrical cardiac signal;
measuring a morphological feature of the repolarization event that is affected by ventricular dyssynchrony; and
detecting ventricular dyssynchrony within the patient based on the morphological feature of the repolarization event, wherein the device is equipped to selectively deliver pacing at any of a plurality of pacing sites and wherein pacing sites are selected so as to reduce ventricular dyssynchrony.

40. The method of claim 39 wherein:
sensing an electrical cardiac signal within the patient includes sensing an intracardiac electrogram (IEGM); and
identifying the ventricular repolarization event within the electrical cardiac signal includes identifying one or more T-waves within the IEGM.

41. The method of claim 30 further including the step of detecting a significant deterioration in ventricular dyssynchrony.

42. The method of claim 41 further including the step of activating a warning device in response to detection of a significant deterioration in ventricular dyssynchrony.

43. The method of claim 30 further including the step of transmitting diagnostic information pertaining to ventricular dyssynchrony to an external system.

44. The method of claim 43 wherein the diagnostic information pertaining to ventricular dyssynchrony sent to the external system includes trending information.

45. A system for use with an implantable medical device for detecting ventricular dyssynchrony, the system comprising:
means for sensing an electrical cardiac signal within the patient in which the device is implanted;
means for identifying a ventricular repolarization event within the electrical cardiac signal;
means for evaluating at least one morphological feature of the repolarization event that is affected by ventricular dyssynchrony, wherein the morphological feature is selected from the group consisting of a number of peaks of an individual T-wave, an area under one or more peaks of an individual T-wave, a number of inflections within an individual T-wave, a slope of an individual T-wave, and combinations thereof;
means for detecting ventricular dyssynchrony within the patient based on the morphological feature of the repolarization event;
means for evaluating the degree of dyssynchrony based on the morphological feature of the repolarization event; and
means for adaptively adjusting the pacing parameters of the implantable medical device based on the morphological feature of the repolarization event.

46. A system for use with an implantable medical device for detecting ventricular dyssynchrony, the system comprising:
- an electrical cardiac signal sensing unit operative to sense electrical cardiac signals within the patient in which the device is implanted;
- a ventricular repolarization event detection unit operative to identify a ventricular repolarization event within the electrical cardiac signal;
- a ventricular repolarization event morphological feature evaluation unit operative to evaluate at least one morphological feature of the repolarization event that is affected by ventricular dyssynchrony, wherein the morphological feature is selected from the group consisting of a number of peaks of an individual T-wave, an area under one or more peaks of an individual T-wave, a number of inflections within an individual T-wave, a slope of an individual T-wave, and combinations thereof;
- a ventricular repolarization-based ventricular dyssynchrony evaluation system operative to detect ventricular dyssynchrony within the patient based on the morphological feature of the repolarization event; and
- a pacing site and timing unit for adaptively adjusting the pacing parameters of the implantable medical device based on the morphological feature of the repolarization event.

47. The system of claim 46 further including a heart failure progression tracking unit operative to track progression of heart failure in the patient based on the degree of ventricular dyssynchrony within the patient.

48. The system of claim 46 further including an implantable warning device operative to generate warnings in response to the detection of ventricular dyssynchrony within the patient.

49. The system of claim 46 further including a telemetry system operative to transmit diagnostic information pertaining to ventricular dyssynchrony to an external system for display.

50. The system of claim 49 wherein the diagnostic information includes trending information.

51. The system of claim 46 wherein the system is implantable.

52. The system of claim 51 wherein the system is a component of the implantable medical device.

* * * * *